(12) United States Patent
Chiu et al.

(10) Patent No.: US 10,709,834 B2
(45) Date of Patent: Jul. 14, 2020

(54) MEDICATION FLUID INFUSION SET COMPONENT WITH INTEGRATED PHYSIOLOGICAL ANALYTE SENSOR, AND CORRESPONDING FLUID INFUSION DEVICE

(71) Applicant: MEDTRONIC MINIMED, INC., Northridge, CA (US)

(72) Inventors: Chia-Hung Chiu, Pasadena, CA (US); Peter Schultz, Chatsworth, CA (US); Gayane R. Voskanyan, Glendale, CA (US); Hsifu Wang, Northridge, CA (US); Rebecca K. Gottlieb, Culver City, CA (US); Kenneth D. Warnock, Manchester, MA (US); Ricardo Juarez Martinez, Somerville, MA (US)

(73) Assignee: Medtronic MiniMed, Inc., Northridge, CA (US)

( * ) Notice: Subject to any disclaimer, the term of this patent is extended or adjusted under 35 U.S.C. 154(b) by 175 days.

(21) Appl. No.: 15/842,800

(22) Filed: Dec. 14, 2017

(65) Prior Publication Data
US 2018/0169322 A1    Jun. 21, 2018

Related U.S. Application Data

(60) Provisional application No. 62/503,282, filed on May 8, 2017, provisional application No. 62/437,536, filed on Dec. 21, 2016.

(51) Int. Cl.
*A61M 5/14* (2006.01)
*A61M 5/142* (2006.01)
(Continued)

(52) U.S. Cl.
CPC .......... *A61M 5/142* (2013.01); *A61B 5/1473* (2013.01); *A61B 5/14532* (2013.01);
(Continued)

(58) Field of Classification Search
CPC . A61B 5/14532; A61B 5/1473; A61B 5/4839; A61M 2005/1587;
(Continued)

(56) References Cited

U.S. PATENT DOCUMENTS

| 4,755,173 A | 7/1988 | Konopka et al. |
| 5,391,250 A | 2/1995 | Cheney, II et al. |

(Continued)

*Primary Examiner* — Imani N Hayman
(74) *Attorney, Agent, or Firm* — Lorenz & Kopf, LLP

(57) ABSTRACT

Disclosed is a medical device component for delivering medication fluid to a patient. The medical device component includes a fluid infusion device to regulate delivery of medication fluid, a body-mountable base unit, and a top cover assembly that is removably couplable to the base unit and to the fluid infusion device. The base unit includes a cannula to deliver medication fluid under the control of the fluid infusion device, and a physiological analyte sensor to measure a physiological characteristic. The base unit also includes an electronics assembly electrically connected to sensor leads to obtain measurements in the analog domain, to convert measurements into digital sensor data, and to communicate conditioned digital sensor data to the fluid infusion device. The top cover assembly is configured to provide both fluid and electrical connections for the base unit, by way of an infusion tube having sensor conductors integrated therein or otherwise associated therewith.

19 Claims, 25 Drawing Sheets

(51) Int. Cl.
*A61M 5/172* (2006.01)
*A61B 5/00* (2006.01)
*A61B 5/145* (2006.01)
*A61B 5/1473* (2006.01)
*A61M 5/20* (2006.01)
*A61M 5/00* (2006.01)
*A61M 5/158* (2006.01)
*A61M 5/145* (2006.01)

(52) U.S. Cl.
CPC ......... *A61B 5/4839* (2013.01); *A61M 5/1413* (2013.01); *A61M 5/14244* (2013.01); *A61M 5/1723* (2013.01); *A61M 5/003* (2013.01); *A61M 5/145* (2013.01); *A61M 5/204* (2013.01); *A61M 2005/1587* (2013.01); *A61M 2005/1726* (2013.01); *A61M 2205/3303* (2013.01)

(58) Field of Classification Search
CPC .. A61M 2005/1726; A61M 2205/3303; A61M 5/003; A61M 5/1413; A61M 5/142; A61M 5/14244; A61M 5/145; A61M 5/1723; A61M 5/204
See application file for complete search history.

(56) References Cited

U.S. PATENT DOCUMENTS

| | | |
|---|---|---|
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,659,980 B2 | 12/2003 | Moberg et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,892,085 B2 | 5/2005 | Melvor et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2007/0123819 A1 | 5/2007 | Mernoe et al. |
| 2010/0160861 A1 | 6/2010 | Causey, III et al. |
| 2011/0233393 A1 | 9/2011 | Hanson et al. |
| 2012/0238849 A1 | 9/2012 | Holtzclaw et al. |
| 2013/0184541 A1 | 7/2013 | Antonio et al. |
| 2015/0314068 A1 | 11/2015 | Alderete, Jr. et al. |

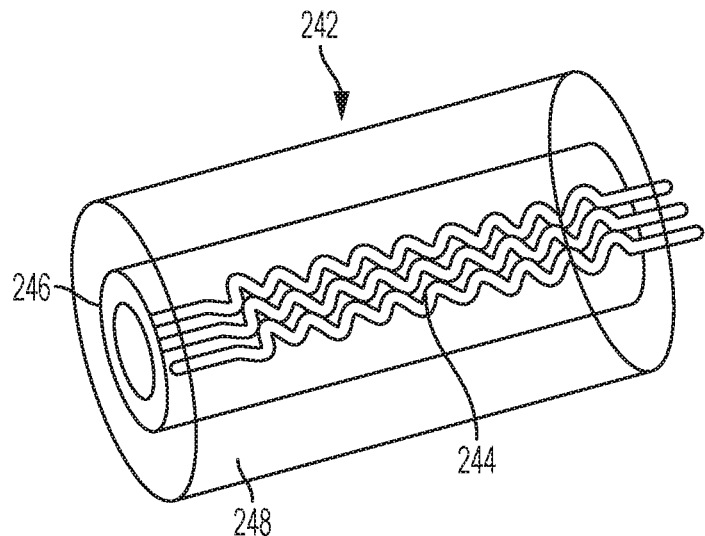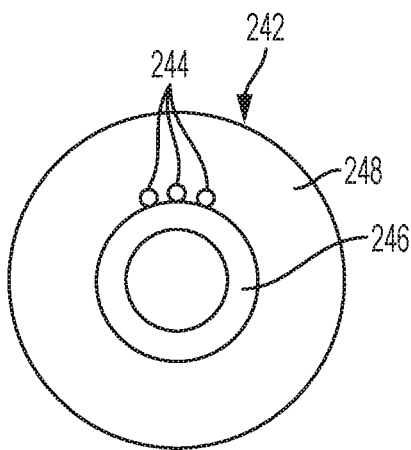
FIG. 6        FIG. 7
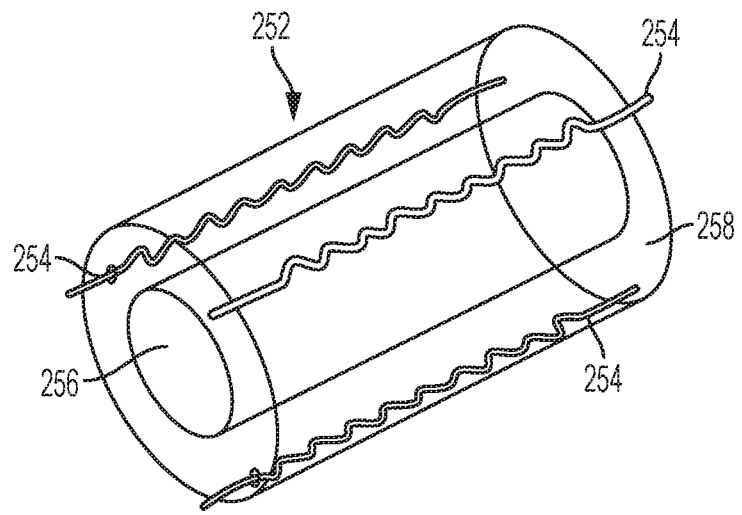
FIG. 8

MEDICATION FLUID INFUSION SET COMPONENT WITH INTEGRATED PHYSIOLOGICAL ANALYTE SENSOR, AND CORRESPONDING FLUID INFUSION DEVICE

CROSS-REFERENCE TO RELATED APPLICATIONS

This application claims the benefit of U.S. provisional patent application No. 62/437,536, filed Dec. 21, 2016, and U.S. provisional application No. 62/503,282, filed May 8, 2017.

TECHNICAL FIELD

Embodiments of the subject matter described herein relate generally to fluid infusion devices, such as medication infusion devices, insulin pumps, and the like. More particularly, embodiments of the subject matter relate to a medication fluid infusion set component having an integrated sensor, and to a medication fluid infusion device that includes such an infusion set component.

BACKGROUND

Portable medical devices are useful for patients that have conditions that must be monitored on a continuous or frequent basis. For example, diabetics are usually required to modify and monitor their daily lifestyle to keep their blood glucose (BG) in balance. Individuals with Type 1 diabetes and some individuals with Type 2 diabetes use insulin to control their BG levels. To do so, diabetics routinely keep strict schedules, including ingesting timely nutritious meals, partaking in exercise, monitoring BG levels daily, and adjusting and administering insulin dosages accordingly.

The prior art includes a number of fluid infusion devices and insulin pump systems that are designed to deliver accurate and measured doses of insulin via infusion sets (an infusion set delivers the insulin through a small diameter tube that terminates at, e.g., a cannula inserted under the patient's skin). In lieu of a syringe, the patient can simply activate the insulin pump to administer an insulin bolus as needed, for example, in response to the patient's high BG level.

A typical fluid infusion pump includes a housing, which encloses a pump drive system, a fluid containment assembly, an electronics system, and a power supply. The pump drive system typically includes a small motor (DC, stepper, solenoid, or other varieties) and drive train components such as gears, screws, and levers that convert rotational motor motion to a translational displacement of a stopper in a reservoir. The fluid containment assembly typically includes the reservoir with the stopper, tubing, and a catheter or infusion set to create a fluid path for carrying medication from the reservoir to the body of a user. The electronics system regulates power from the power supply to the motor. The electronics system may include programmable controls to operate the motor continuously or at periodic intervals to obtain a closely controlled and accurate delivery of the medication over an extended period.

The prior art also includes a variety of physiological analyte sensors that are designed to measure an analyte of a patient. For example, continuous glucose sensors employ subcutaneous glucose sensor technology that facilitates ongoing monitoring of blood glucose levels. Continuous glucose sensors may utilize wireless data communication techniques to transmit data indicative of the blood glucose levels to a portable infusion pump, a glucose monitor device, and/or other receiving devices. Thus, in a typical insulin pump system, the patient might wear both an infusion set (for the delivery of insulin) and a glucose sensor-transmitter.

BRIEF SUMMARY

This disclosure relates to a medical device component for delivering medication fluid to a patient. Embodiments of the medical device component include a body-mountable base unit and a top cover assembly that is removably couplable to the base unit. The base unit includes: a base structure; a body-insertable cannula coupled to the base structure, the cannula accommodating delivery of medication fluid to the patient; a self-sealing septum coupled to the base structure to fluidly seal an end of the cannula; a body-insertable physiological analyte sensor coupled to the base structure, the sensor facilitating measurement of a physiological characteristic of the patient, and the sensor having a plurality of sensor leads; and an electronics assembly coupled to the base structure. The electronics assembly is electrically connected to the sensor leads to obtain measurements of the physiological characteristic in an analog domain. The electronics assembly includes a digital processing circuit to convert measurements of the physiological characteristic from the analog domain into digital sensor data, to digitally process the digital sensor data into conditioned digital sensor data, and to communicate the conditioned digital sensor data to a fluid infusion device associated with the medical device component. The top cover assembly includes: a lid structure that releasably mates with the base structure, the lid structure having an interior space defined by an inner surface of the lid structure; an infusion tube coupled to the inner surface of the lid structure and terminating within the interior space; a tubing connector fluidly coupled to the infusion tube, the tubing connector having a distal end that penetrates the self-sealing septum to establish a fluid delivery flow path from the infusion tube to the cannula when the top cover assembly is coupled to the body-mountable base unit; a plurality of sensor conductors carried by or integrated with the infusion tube, the sensor conductors terminating within the interior space; and an electrical interconnect assembly coupled to the inner surface of the lid structure. The electrical interconnect assembly establishes electrical connectivity between the sensor conductors and the electronics assembly when the top cover assembly is coupled to the body-mountable base unit, to facilitate communication of the conditioned digital sensor data from the electronics assembly to the fluid infusion device.

This disclosure also relates to a medical device component for delivering medication fluid to a patient. Embodiments of the medical device component include: a fluid infusion device to regulate delivery of medication fluid; a base unit; and a top cover assembly that is removably couplable to the base unit. The base unit includes: a cannula that accommodates delivery of medication fluid as controlled by the fluid infusion device; a self-sealing septum that fluidly seals an end of the cannula; a physiological analyte sensor that facilitates measurement of a physiological characteristic, the sensor having a plurality of sensor leads; and an electronics assembly electrically connected to the sensor leads to obtain measurements of the physiological characteristic in an analog domain. The electronics assembly includes a digital processing circuit to convert measurements of the physiological characteristic from the analog domain into digital sensor data, to digitally process the digital sensor data into conditioned digital sensor data, and to communicate the conditioned digital sensor data to the fluid infusion device. The top cover assembly includes: a lid structure that releasably mates with the base unit, the lid structure having an interior space defined by an inner surface of the lid structure; an infusion tube coupled to the inner surface of the lid structure and terminating within the interior space; a tubing connector fluidly coupled to the infusion tube, the tubing connector having a distal end that penetrates the self-sealing septum to establish a fluid delivery flow path from the infusion tube to the cannula when the top cover assembly is coupled to the base unit; a plurality of sensor conductors terminating within the interior space; and an electrical interconnect assembly coupled to the inner surface of the lid structure. The electrical interconnect assembly establishes electrical connectivity between the sensor conductors and the electronics assembly when the top cover assembly is coupled to the base unit, to facilitate communication of the conditioned digital sensor data from the electronics assembly to the fluid infusion device.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

FIG. 6 is a partially phantom perspective view of an exemplary embodiment of an infusion tube having sensor conductors (in the form of crimped wires) integrated therein;

FIG. 7 is an end view of the infusion tube shown in FIG. 6;

FIG. 8 is a partially phantom perspective view of another exemplary embodiment of an infusion tube having sensor conductors (in the form of crimped wires) integrated therein;

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

The subject matter described here relates to a fluid infusion device of the type used to treat a medical condition of a patient. The infusion device is used for infusing medication fluid into the body of a user. The non-limiting examples described below relate to a medical device used to treat diabetes (more specifically, an insulin pump), although embodiments of the disclosed subject matter are not so limited. Accordingly, the infused medication fluid is insulin in certain embodiments. In alternative embodiments, however, many other fluids may be administered through infusion such as, but not limited to, disease treatments, drugs to treat pulmonary hypertension, iron chelation drugs, pain medications, anti-cancer treatments, medications, vitamins, hormones, or the like.

For the sake of brevity, conventional features and technologies related to infusion system operation, insulin pump and/or infusion set operation, blood glucose sensing and monitoring, sensor signal processing, and other functional aspects of the fluid infusion system (and the individual operating components of the system) may not be described in detail here. Examples of fluid infusion devices, analyte sensors, and related components may be of the type described in, but not limited to, U.S. Pat. Nos. 6,659,980;

6,892,085; and 7,621,893 (which are incorporated by reference herein). Exemplary embodiments of an infusion set component with integrated analyte sensor conductors are disclosed in United States patent publication number 2012/0238849 (which is incorporated by reference herein). An exemplary embodiment of a fluid infusion device is disclosed in United States patent publication number 2015/0314068 (which is incorporated by reference herein).

Figure 1:
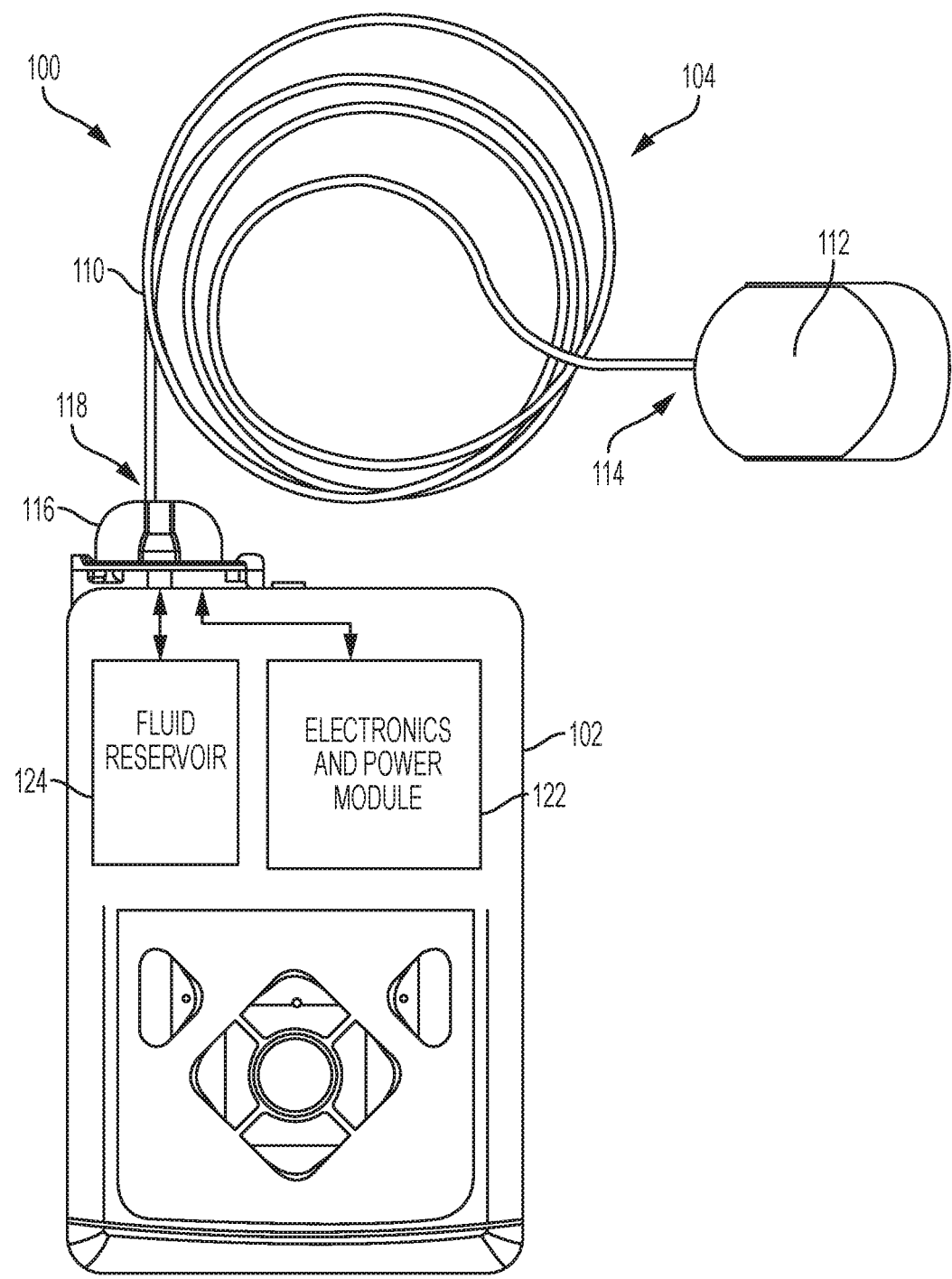
FIG. 1 is a plan view of an exemplary embodiment of a medical device component that includes a fluid infusion device.

FIG. 1 is a schematic plan view of an exemplary embodiment of a medical device component 100. The medical device component 100 includes two primary elements: a fluid infusion device 102 (e.g., an insulin pump) and an infusion set component 104, which can be coupled to the fluid infusion device 102 as depicted in FIG. 1. This particular embodiment of the infusion set component 104 includes, without limitation: an infusion tube 110; a medical device component realized in the form of a combined infusion-sensor unit 112 coupled to one end 114 of the infusion tube 110; and a connector assembly 116 coupled to the other end 118 of the infusion tube 110. The fluid infusion device 102 is designed to be carried or worn by the patient, and the infusion set component 104 terminates at the combined infusion-sensor unit 112 such that the fluid infusion device 102 can deliver medication fluid to the body of the patient in a controlled and regulated manner via the infusion tube 110. Moreover, the combined infusion-sensor unit 112 cooperates with the fluid infusion device 102 to sense, measure, or detect an analyte of the patient (such as blood glucose), as described in more detail below. The fluid infusion device 102 may leverage a number of conventional features, components, elements, and characteristics of existing fluid infusion devices. For example, the fluid infusion device 102 may incorporate some of the features, components, elements, and/or characteristics described in U.S. Pat. No. 7,621,893 and United States patent publication number 2015/0314068, the relevant content of which is incorporated by reference herein.

The fluid infusion device 102 operates to regulate the delivery of medication fluid to the patient. The fluid infusion device 102 generally includes an electronics and power module 122 that controls a mechanism (not shown) to actuate a fluid reservoir 124 housed in the body of the fluid infusion device 102. When realized as an insulin infusion pump, the fluid infusion device 102 controls and manages the delivery of insulin to manage blood glucose levels of the patient. The fluid infusion device 102 accommodates the fluid reservoir 124 that contains the medication fluid to be delivered to the user. The infusion tube 110 represents the fluid flow path that couples the fluid reservoir 124 to the combined infusion-sensor unit 112. When installed as depicted in FIG. 1, the infusion tube 110 extends from the fluid infusion device 102 to the combined infusion-sensor unit 112, which in turn provides a fluid pathway to the body of the patient. For the illustrated embodiment, the connector assembly 116 is realized as a removable reservoir cap (or fitting) that is suitably sized and configured to accommodate replacement of fluid reservoirs 124 (which are typically disposable) as needed. In this regard, the reservoir cap is designed to accommodate the fluid path from the fluid reservoir 124 to the infusion tube 110. Accordingly, the fluid reservoir 124 is fluidly coupled to the infusion tube 110, by way of the connector assembly 116.

In certain implementations, a number of sensor conductors are carried by, integrated with, or are otherwise provided by the infusion tube 110. In this regard, the infusion tube 110 can be fabricated with electrical sensor conductors embedded therein to support the operation of a body-insertable physiological analyte sensor located at the combined infusion-sensor unit 112. In accordance with the embodiments presented here, the sensor conductors are suitably configured and arranged to provide operating power from the fluid infusion device 102 to the combined infusion-sensor unit 112. In addition, the sensor conductors are suitably configured and arranged to transmit digital data from the combined infusion-sensor unit 112 to the fluid infusion device 102. In this regard, the infusion tube 110 performs at least three primary functions during normal operation of the fluid infusion device 102: (1) deliver medication fluid to the patient; (2) provide operating voltage to the combined infusion-sensor unit 112; and (3) convey digital data (e.g., digital sensor data obtained from the analyte sensor of the combined infusion-sensor unit 112) to the fluid infusion device 102.

In practice, the electronics and power module 122 of the fluid infusion device 102 may be used to generate voltage, current, and/or electrical signals for use by the combined infusion-sensor unit 112 as needed, and the electronics and power module 122 may also be used to detect or receive digital data that represents the measured analyte of the patient. In this regard, the electronics and power module 122 is electrically connected to contacts or terminals of the connector assembly 116, wherein the contacts or terminals correspond to the sensor conductors of the infusion tube 110.

Figure 2:
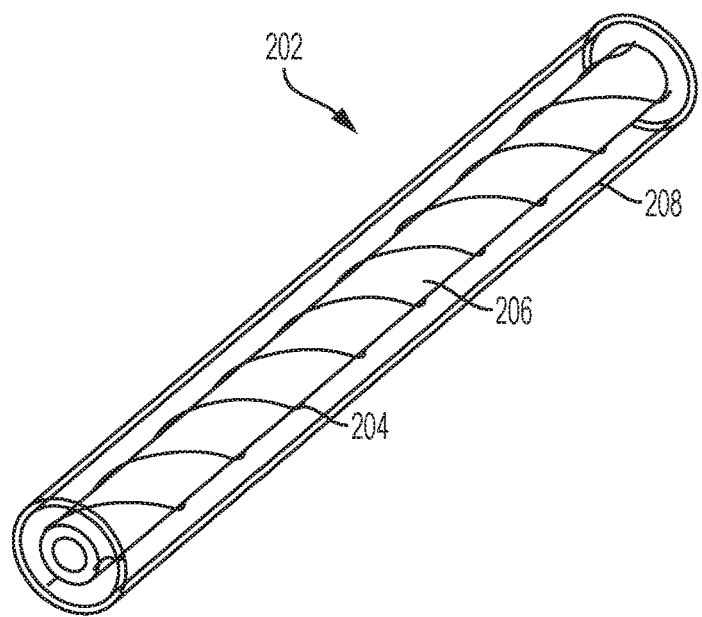
FIG. 2 is a partially phantom perspective view of an exemplary embodiment of an infusion tube having sensor conductors (in the form of wires) integrated therein.
Figure 3:
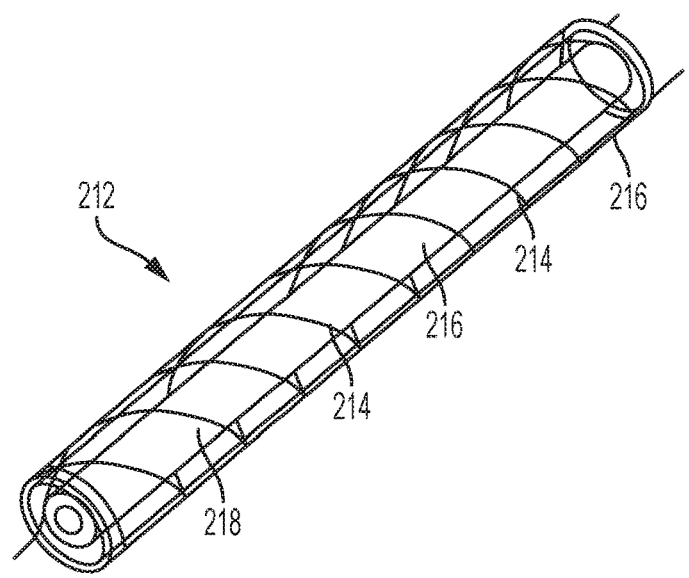
FIG. 3 is a partially phantom perspective view of another exemplary embodiment of an infusion tube having sensor conductors (in the form of wires) integrated therein.
Figure 4:
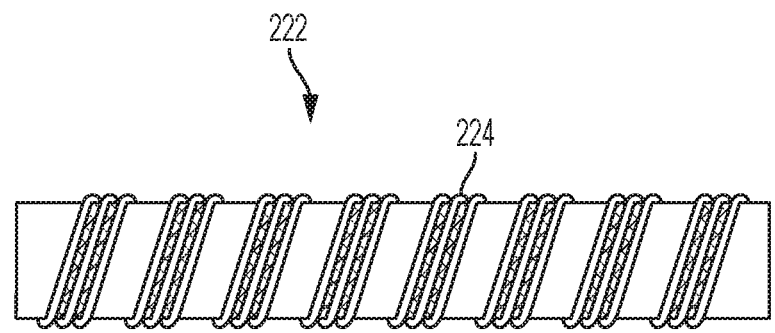
FIG. 4 is a partially phantom perspective view of an exemplary embodiment of an infusion tube having sensor conductors (in the form of a ribbon cable) integrated therein.
Figure 5:
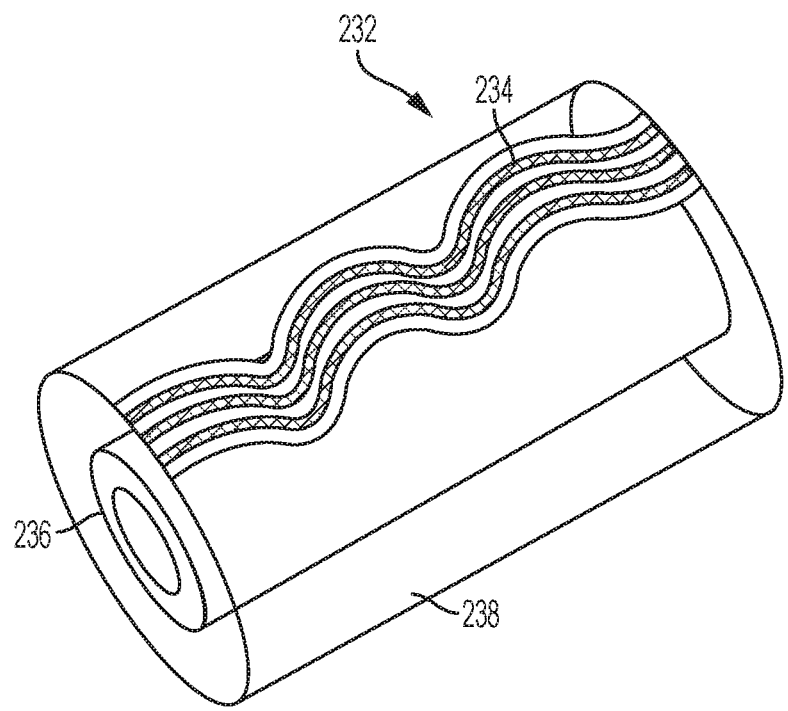
FIG. 5 is a partially phantom perspective view of an exemplary embodiment of an infusion tube having sensor conductors (in the form of a flexible circuit arrangement) integrated therein.

FIGS. 2-8 show various infusion tube embodiments, each having sensor conductors integrated therein. More specifically: FIG. 2 is a partially phantom perspective view of an exemplary embodiment of an infusion tube having sensor conductors (in the form of wires) integrated therein; FIG. 3 is a partially phantom perspective view of another exemplary embodiment of an infusion tube having sensor conductors (in the form of wires) integrated therein; FIG. 4 is a partially phantom perspective view of an exemplary embodiment of an infusion tube having sensor conductors (in the form of a ribbon cable) integrated therein; FIG. 5 is a partially phantom perspective view of an exemplary embodiment of an infusion tube having sensor conductors (in the form of a flexible circuit arrangement) integrated therein; FIG. 6 is a partially phantom perspective view of an exemplary embodiment of an infusion tube having sensor conductors (in the form of crimped wires) integrated therein; FIG. 7 is an end view of the infusion tube shown in FIG. 6; and FIG. 8 is a partially phantom perspective view of another exemplary embodiment of an infusion tube having sensor conductors (in the form of crimped wires) integrated therein. It should be appreciated that FIGS. 2-8 depict a number of suitable implementations of the infusion tube 110 in a non-limiting and non-exhaustive manner. An embodiment of the infusion set component 104 can incorporate an infusion tube 110 having a different configuration and/or arrangement of sensor conductors if so desired.

In general, the infusion tube 110 is fabricated with electrical sensor conductors integrated therein or carried thereon to support the operation of the sensor located at the combined infusion-sensor unit 112. The infusion tube 110 is formed from an appropriate type and composition of tubing material, which is fabricated with an interior fluid canal defined therein. The interior fluid canal provides a fluid pathway for the medication fluid. The tubing material may be any flexible, tough, and lightweight material such as, without limitation: a polyethylene polymer; a polyurethane polymer; or the like. For the exemplary embodiment described here, the tubing material is a molded or extruded concentric construction, which may include multiple concentric layers or a single layer. Moreover, the infusion tube 110 is formed from a material (or materials) that is compatible with the particular type of medication fluid or fluids to be delivered, such as insulin medication fluid.

The infusion tube 202 depicted in FIG. 2 includes three sensor conductors 204 wrapped around an inner tubing layer 206 (although alternate embodiments may include more or less than three sensor conductors). For this particular embodiment, the three sensor conductors 204 are utilized as a power conductor, a ground conductor, and a data conductor. Accordingly, the sensor conductors 204 provide operating power to the combined infusion-sensor unit 112, and also accommodate the transmission of digital data (representing the analyte sensor measurements) from the combined infusion-sensor unit 112 to the fluid infusion device 102. Notably, the sensor conductors 204 are not intended to convey analog sensor information because the combined infusion-sensor unit 112 performs analog-to-digital conversion of the analog sensor values, performs digital data conditioning on the converted digital data, and sends the conditioned sensor data to the fluid infusion device 102 in the digital domain.

The sensor conductors 204 may be realized as thin cooper wires, metal traces, or conductive filaments. An outer tubing layer 208 of the infusion tube 202 surrounds and insulates the sensor conductors 204. Alternatively, the sensor conductors 204 can be embedded in a layer of the tubing material. In this regard, the tubing material may be composed of an electrically insulating material to electrically insulate each of the sensor conductors. In such an embodiment, the sensor conductors need not be individually surrounded by an insulating sleeve or casing. In practice, the sensor conductors could be molded within the tubing material such that they are spaced apart from one another as shown in FIG. 2. In other embodiments, insulated sensor conductors (e.g., wires covered in an insulating material) can be wrapped overlying the outermost surface of the infusion tube 202. Such an arrangement can have manufacturing and/or assembly advantages related to establishing electrical connections for the wires.

The infusion tube 212 shown in FIG. 3 is similar to the infusion tube 202 depicted in FIG. 2, however, the three sensor conductors 214 are wrapped around (and embedded within) the outer tubing layer 216. The infusion tube 212 also includes a concentric inner tubing layer 218 surrounded by the outer tubing layer 216 and, therefore, surrounded by the sensor conductors 214.

The infusion tube 222 shown in FIG. 4 includes sensor conductors that are realized in the form of a ribbon cable 224. For this example, the ribbon cable 224 includes three adjacent conductors, grouped together but electrically insulated from each other. FIG. 4 depicts the ribbon cable 224 wrapped around a tubing layer 226. In practice, the ribbon cable 224 can serve as the outermost layer of the infusion tube 222 due to its self-insulated nature. Alternatively, the infusion tube 222 can include an outer tubing layer (not shown) that is formed overlying the ribbon cable 224.

The infusion tube 232 shown in FIG. 5 includes sensor conductors that are realized in the form of a flexible circuit arrangement 234. In accordance with the illustrated embodiment, the flexible circuit arrangement 234 has a bent "wave" shape that allows a relatively flat circuit design to stretch and move easily when the infusion tube 232 is bent. The flexible circuit arrangement 234 is arranged in a flat orientation, and it can be embedded in the inner tubing layer 236, embedded in the outer tubing layer 238 (as shown), or positioned between the inner and outer tubing layers 236, 238.

The infusion tube 242 shown in FIG. 6 and FIG. 7 includes sensor conductors that are realized in the form of crimped wires 244 that terminate in relatively straight ends. The crimped wires 244 can easily stretch and compress to accommodate bending of the infusion tube 242. In accordance with the illustrated embodiment, the crimped wires 244 are arranged side by side, and they can be embedded in the inner tubing layer 246, embedded in the outer tubing layer 248, or positioned between the inner and outer tubing layers 246, 248. Notably, the straight and relatively flat layout of the ends of the crimped wires 244 (see FIG. 7) makes it easy to physically and electrically connect the crimped wires 244 to a circuit board, an interconnect assembly, contact pads, or the like.

The infusion tube 252 depicted in FIG. 8 also includes sensor conductors implemented in the form of crimped wires 254. The infusion tube 252 is similar to the infusion tube 242 shown in FIG. 7. The illustrated embodiment of the infusion tube 252, however, includes a spaced-apart arrangement of the crimped wires 254. For example, the crimped wires 254 can be oriented 120 degrees apart to balance the mass of the infusion tube 252. The crimped wires 254 can be embedded in the inner tubing layer 256, embedded in the outer tubing layer 258, or positioned between the inner and outer tubing layers 256, 258.

FIG. 1 depicts the combined infusion-sensor unit 112 in a simplified schematic form. An exemplary embodiment of the infusion-sensor unit 112 will now be described with reference to FIGS. 9-20. It should be appreciated that these figures merely depict one possible implementation, and that alternative embodiments of the infusion-sensor unit 112 can be realized if so desired. FIGS. 9-20 illustrate an embodiment of the infusion-sensor unit 112 that includes two primary subcomponents: a body-mountable base unit 302; and a top cover assembly 304 that is removably couplable to the base unit 302. The base unit 302 is designed to be affixed to the skin of the patient and worn in that manner for a designated period of time, e.g., up to several days, a week, or the like. An appropriate insertion/installation mechanism can be used to mount the base unit 302 onto the skin and to deploy insertion needles to insert the infusion cannula and the analyte sensor into the skin. The top cover assembly 304 mates with, and is secured to, the base unit 302 in a way that establishes the necessary mechanical, electrical, and fluid connections (as described in more detail below).

Figure 9:
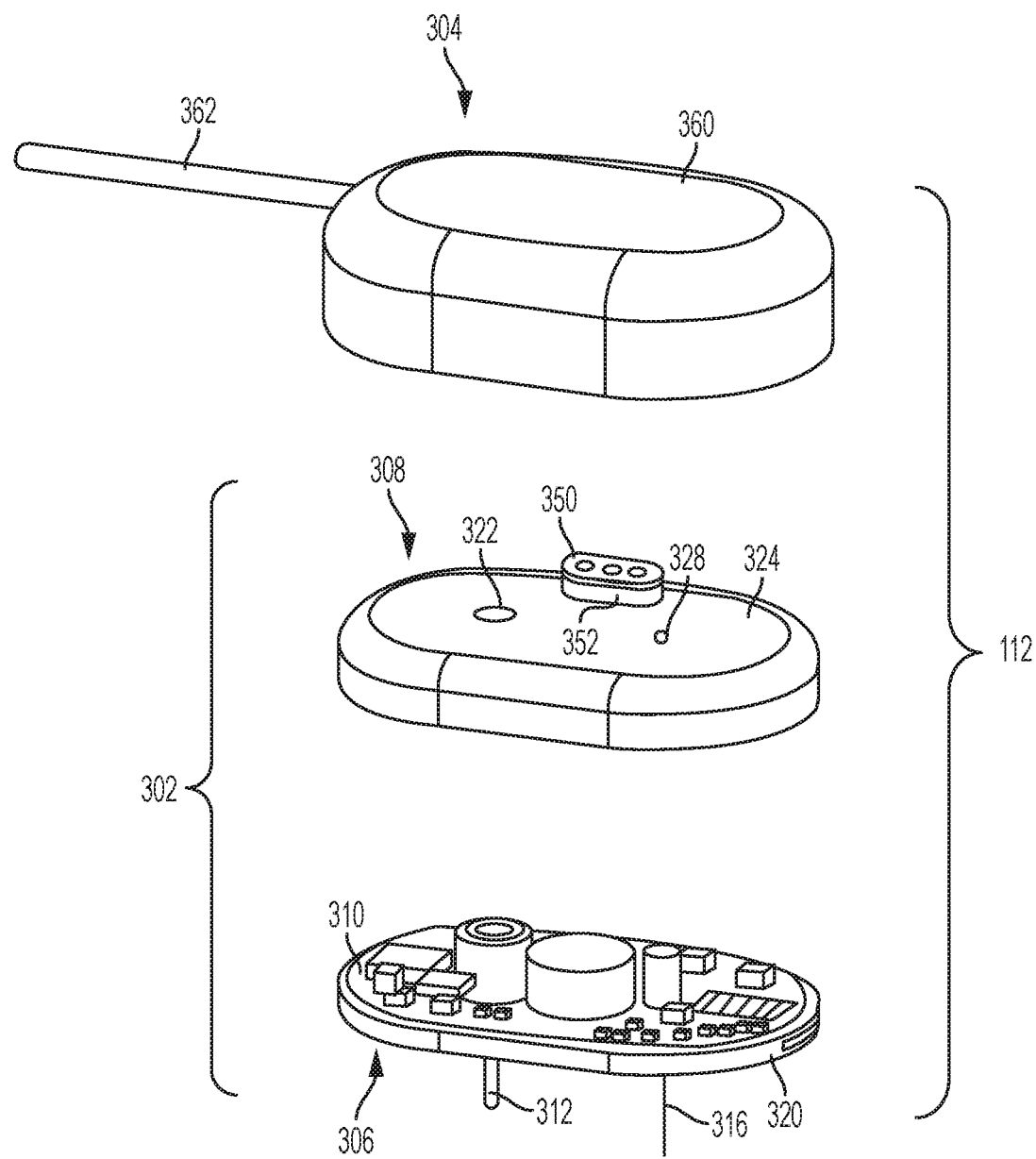
FIG. 9 is an exploded perspective view of an exemplary embodiment of a combined infusion-sensor unit suitable for use with the medical device component shown in FIG. 1.
Figure 10:
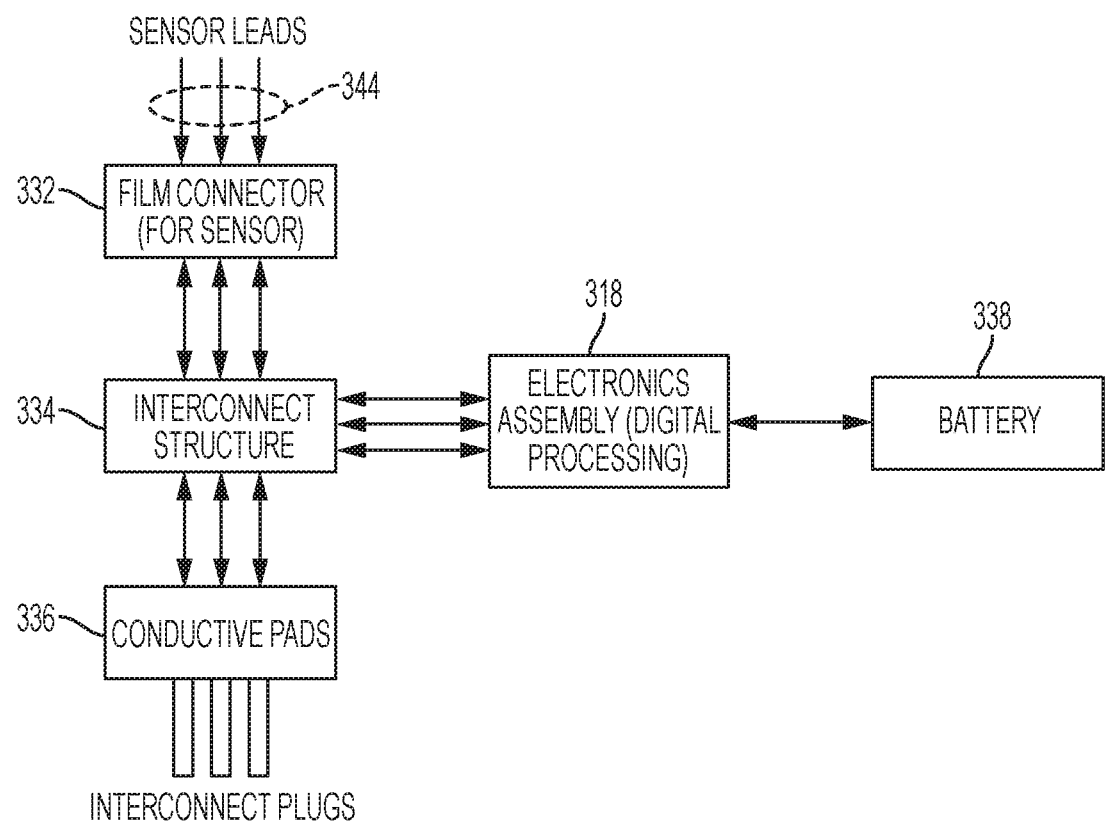
FIG. 10 is a schematic block diagram that depicts certain features and elements of the combined infusion-sensor unit.
Figure 11:
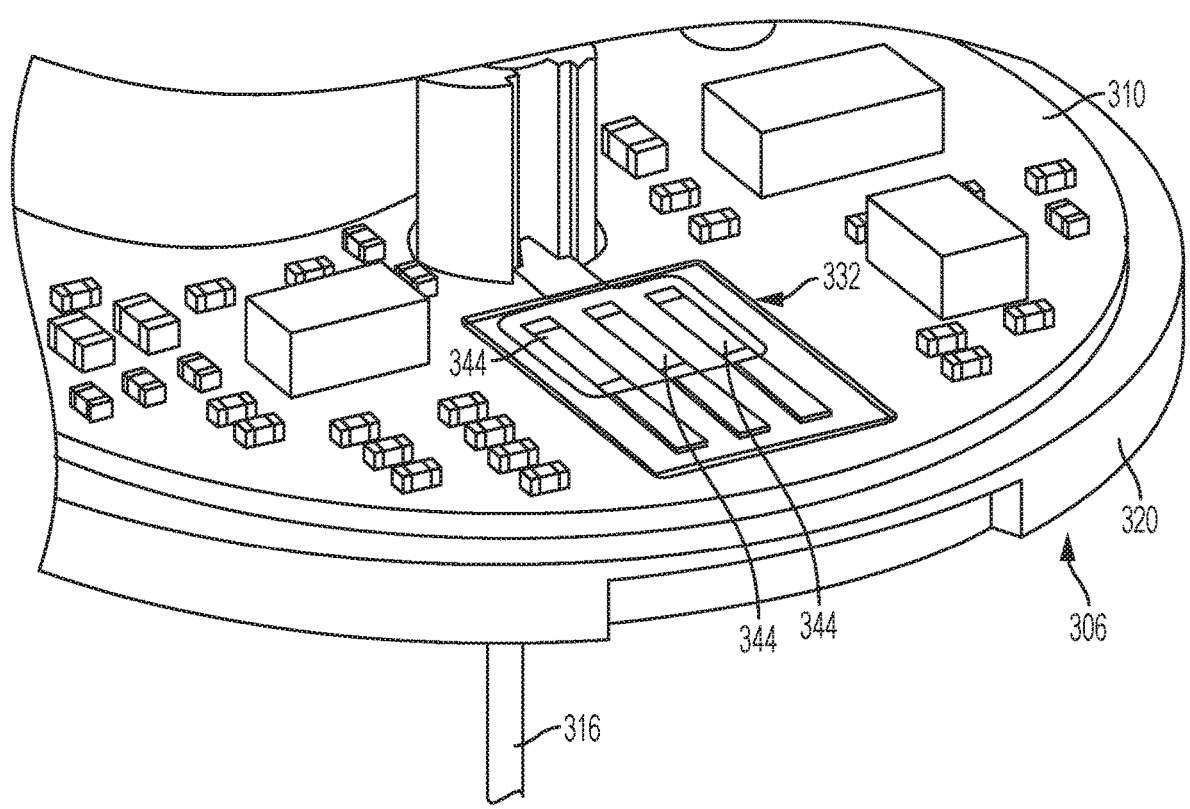
FIG. 11 is a perspective view of a portion of the combined infusion-sensor unit.
Figure 12:
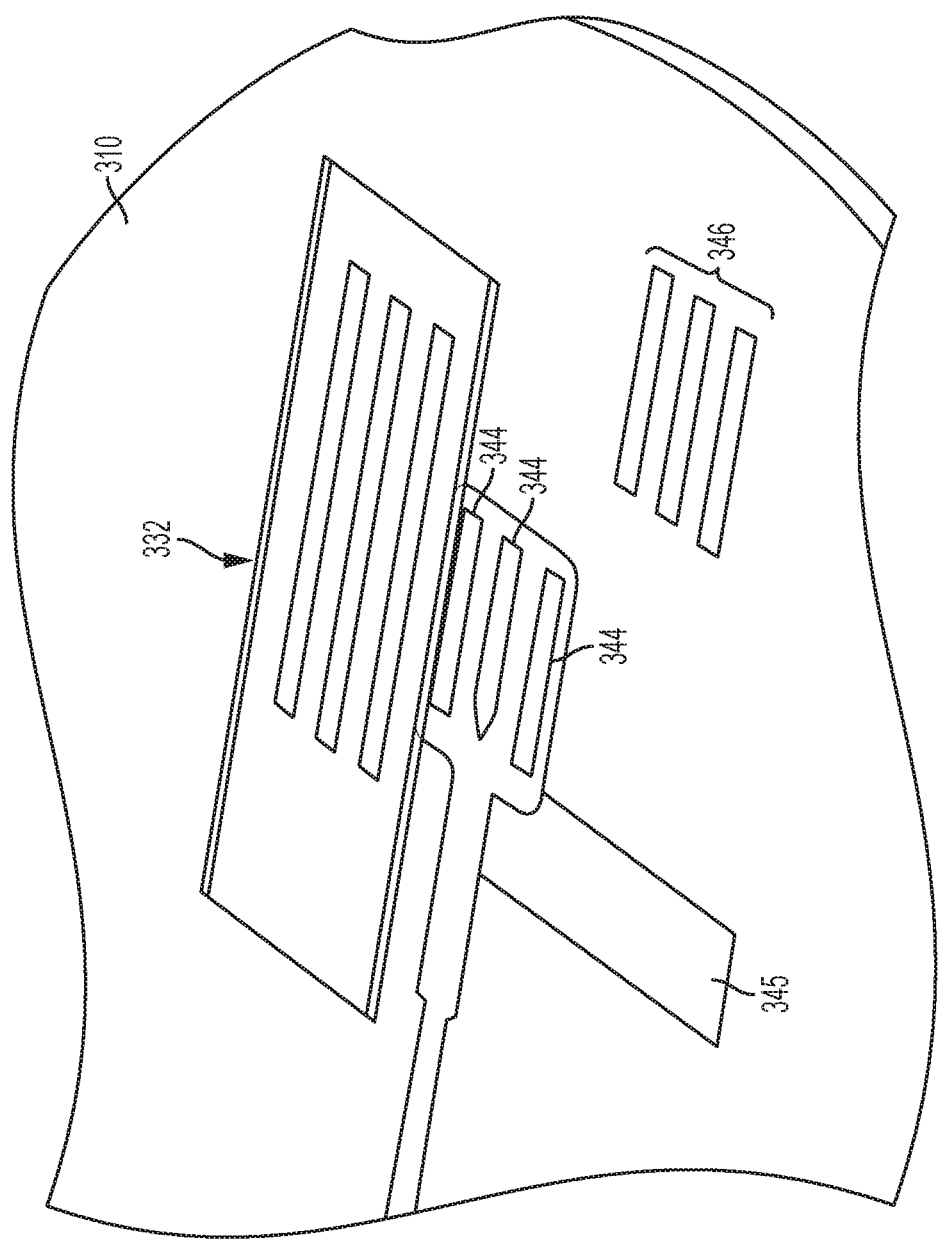
FIG. 12 is an exploded perspective view of a film connector of the combined infusion-sensor unit.
Figure 13:
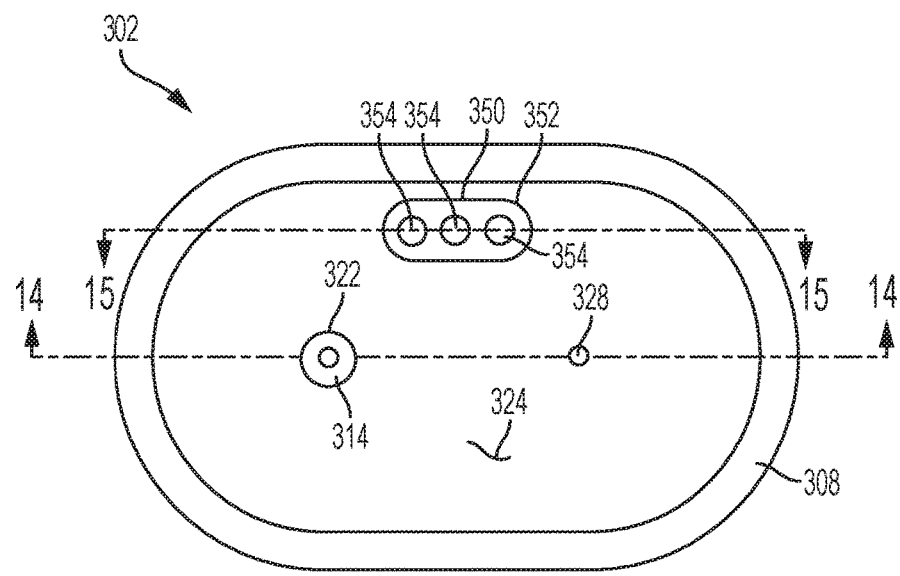
FIG. 13 is a top view of a body-mountable base unit of the combined infusion-sensor unit.
Figure 14:
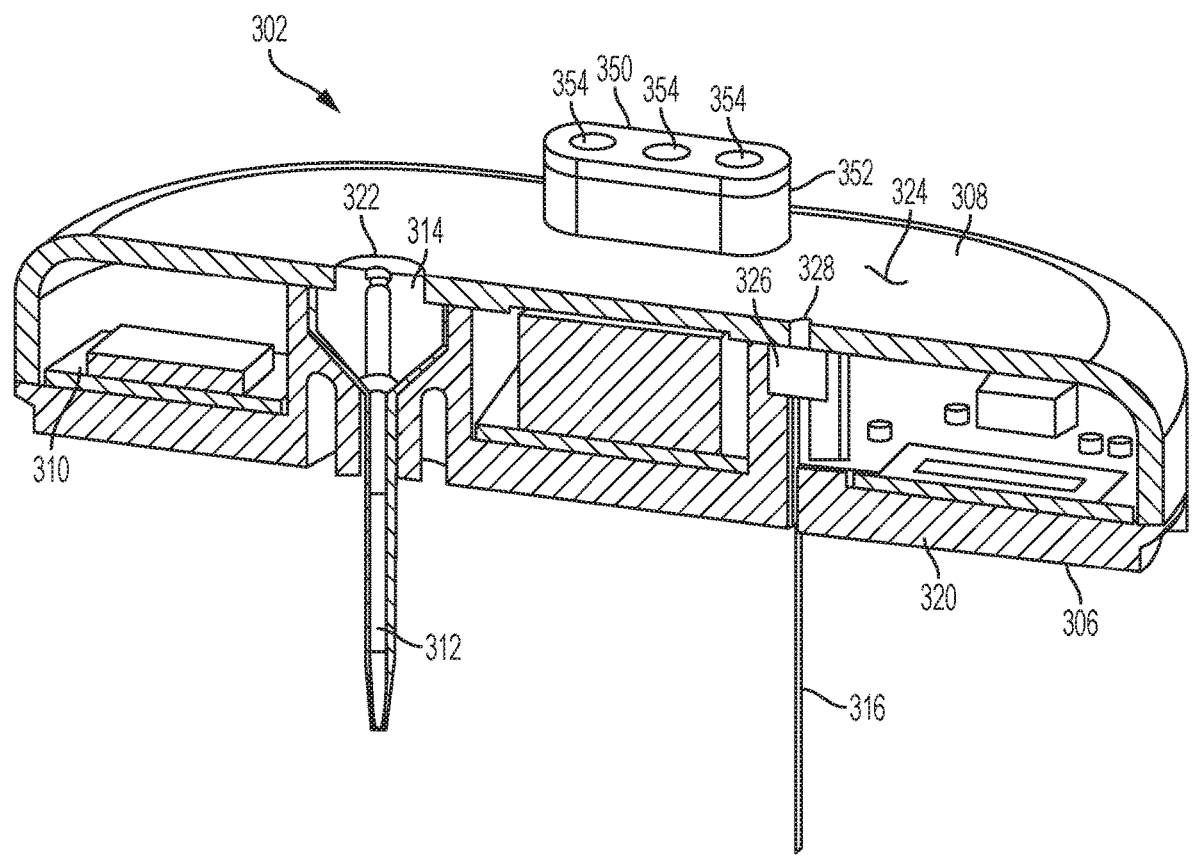
FIG. 14 is a perspective cross-sectional view of the body-mountable base unit, taken from line 14-14 of FIG. 13.
Figure 15:
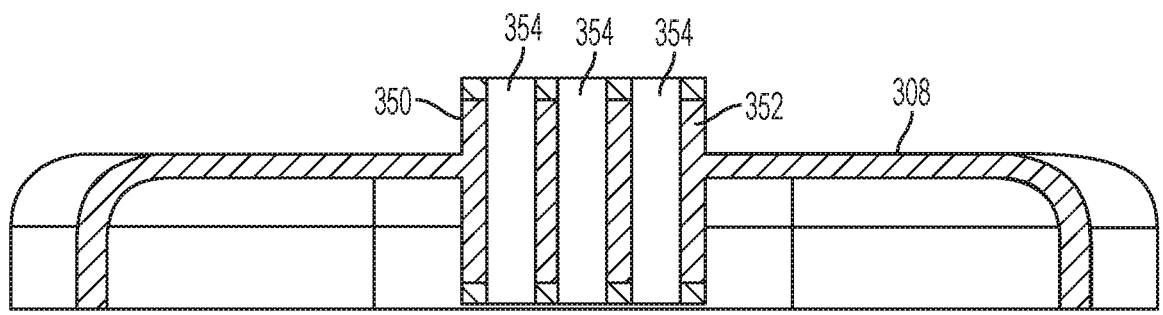
FIG. 15 is a cross-sectional view of a portion of the body-mountable base unit, taken from line 15-15 of FIG. 13.
Figure 16:
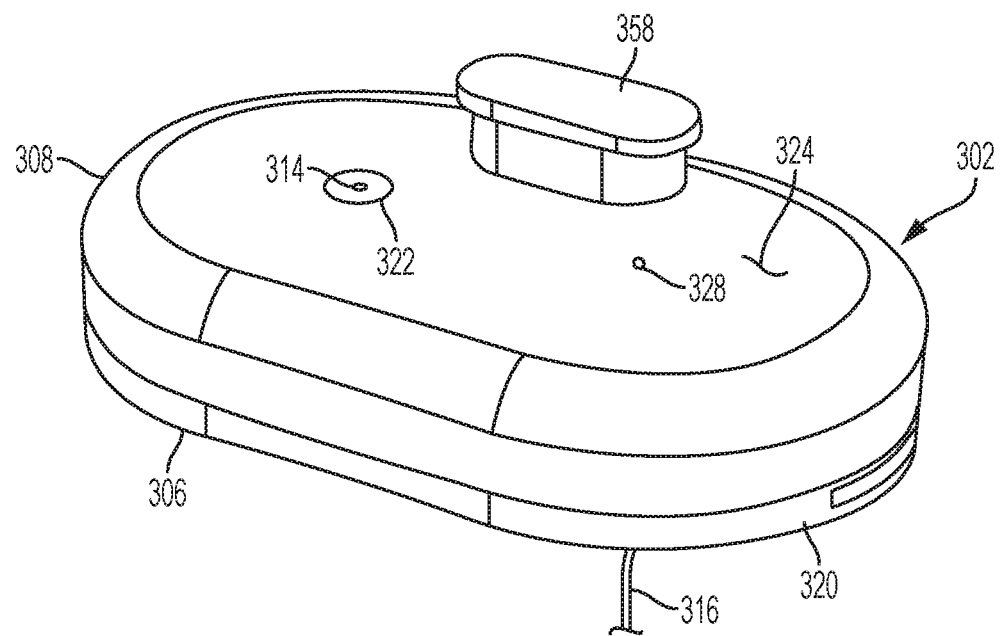
FIG. 16 is a top perspective view of the body-mountable base unit, with a protective cap installed thereon.
Figure 17:
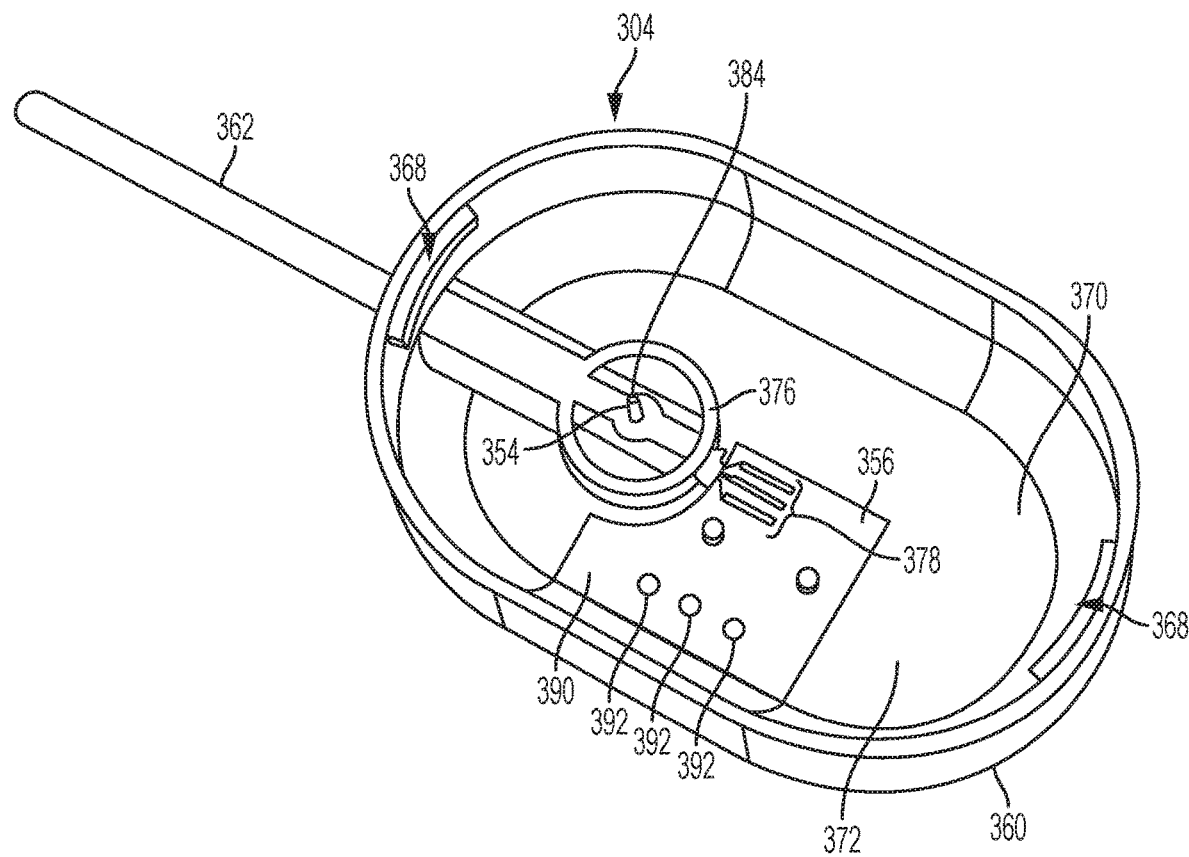
FIG. 17 is a bottom perspective view of a top cover assembly of the combined infusion-sensor unit.
Figure 18:
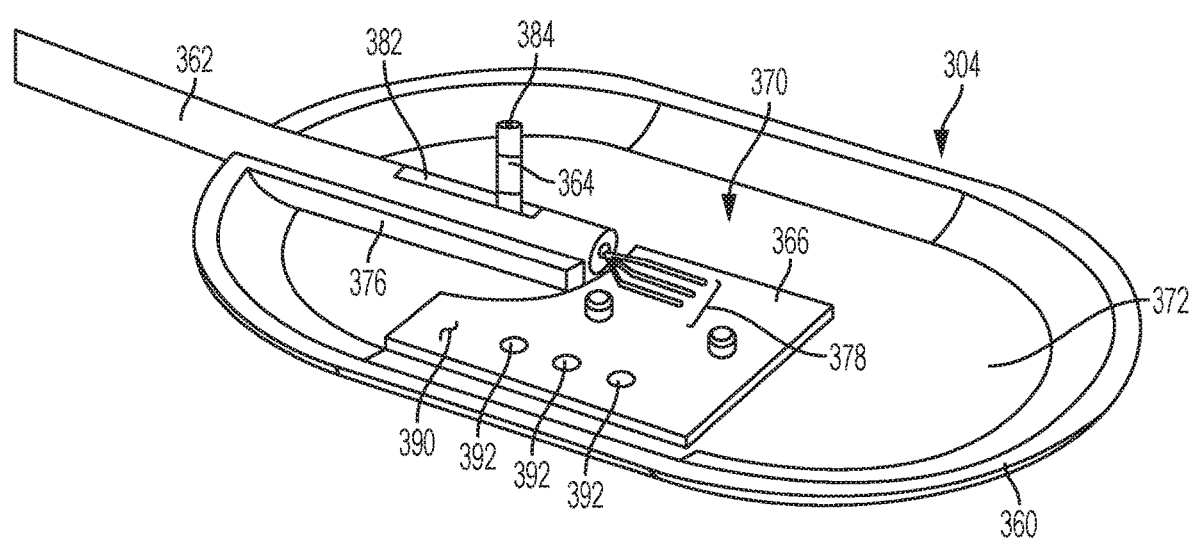
FIG. 18 is a perspective view of the top cover assembly, with a portion removed to depict certain features.
Figure 19:
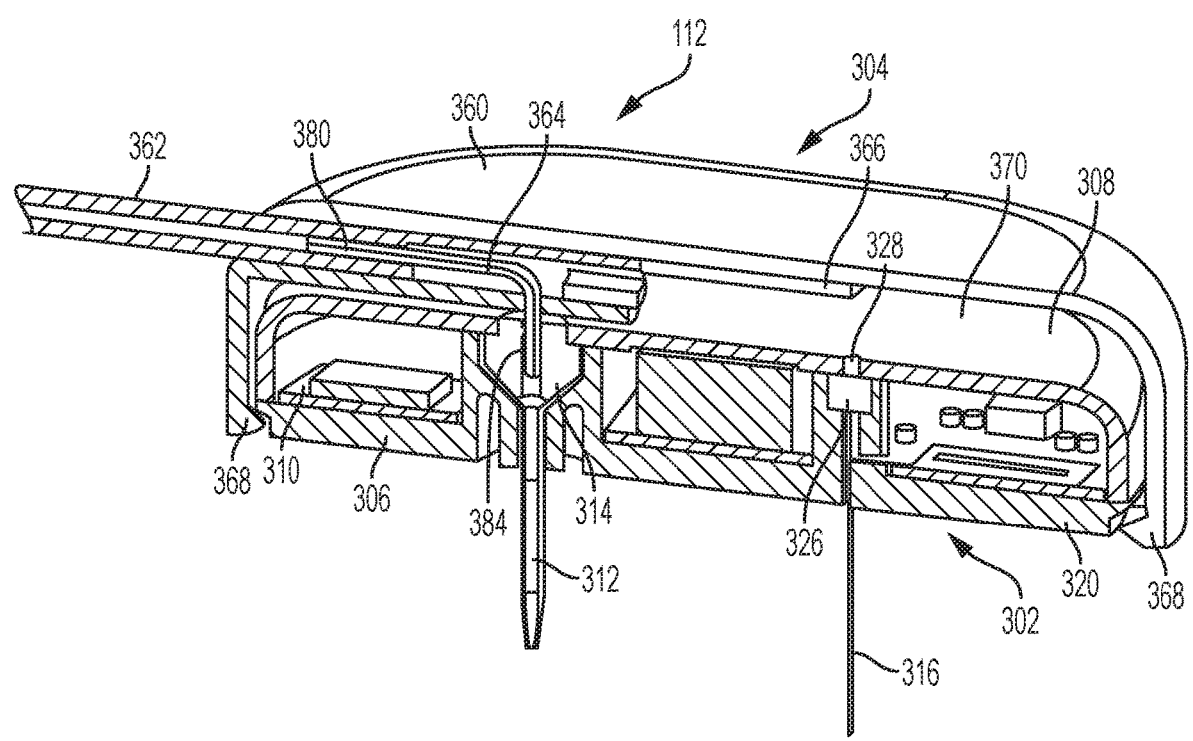
FIGS. 19 and 20 are perspective cross-sectional views of the combined infusion-sensor unit.
Figure 20:
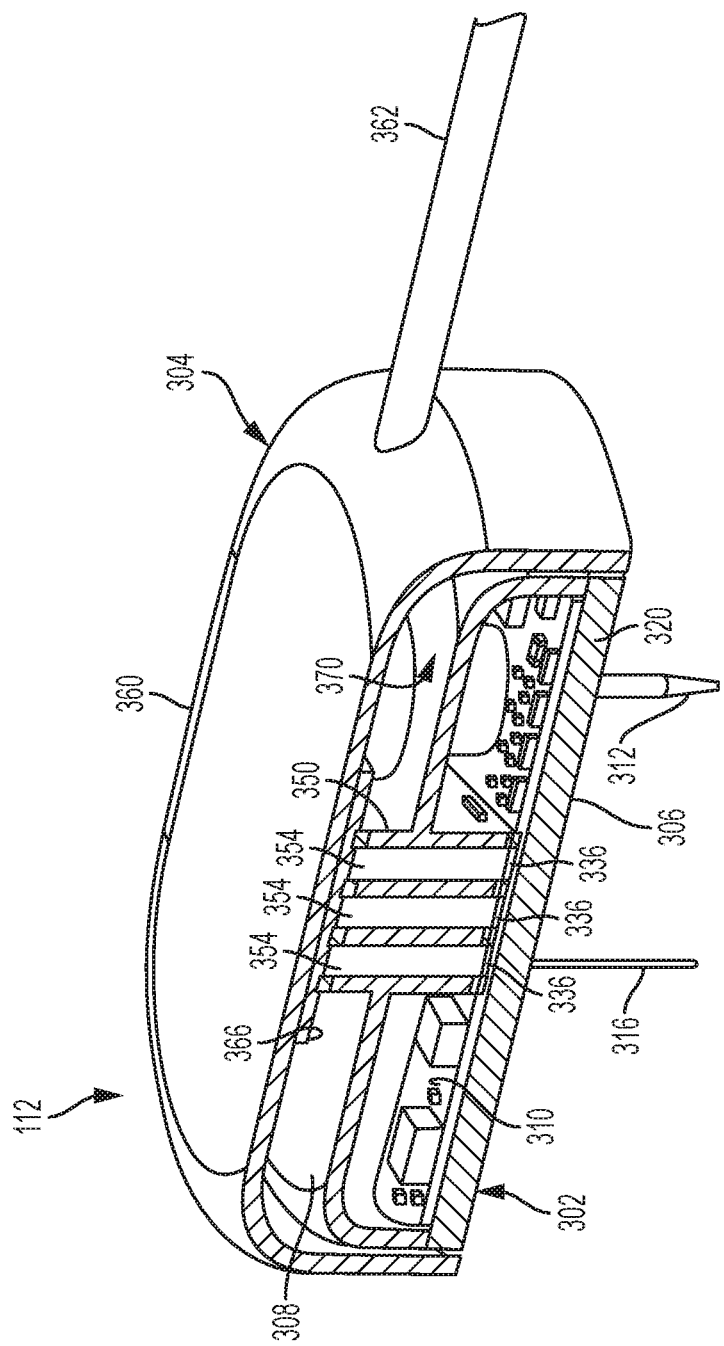

FIG. 9 is an exploded perspective view of the infusion-sensor unit 112, and FIG. 10 is a schematic block diagram that depicts certain features and elements of the infusion-sensor unit 112. FIG. 11 is a perspective view of a portion of the infusion-sensor unit 112, and FIG. 12 is an exploded perspective view of a film connector suitable for use on a circuit board of the infusion-sensor unit 112. FIG. 13 is a top view of the base unit 302, FIG. 14 is a perspective cross-sectional view of the base unit 302, taken from line 14-14 of FIG. 13, and FIG. 15 is a cross-sectional view of a portion of base unit 302, taken from line 15-15 of FIG. 13. FIG. 16 is a top perspective view of the base unit 302, with a protective cap installed thereon, FIG. 17 is a bottom perspective view of the top cover assembly 304, and FIG. 18 is a bottom perspective view of a portion of the top cover assembly 304. FIGS. 19 and 20 are perspective cross-sectional views of the combined infusion-sensor unit 112.

The base unit 302 includes a base structure 306 and a lid assembly 308, which is affixed and sealed to the base structure 306. The lid assembly 308 is not intended to be removed from the base structure 306—the lid assembly 308 protects the components carried by the base structure 306 from the ingress of water, fluid, dust, dirt, and other potential contaminants. The base structure 306 includes or cooperates with the primary devices, components, and elements of the infusion-sensor unit 112. For this particular embodiment, the base unit 302 includes at least the following items, without limitation: a circuit board 310; a body-insertable cannula 312 coupled to the base structure 306, wherein the cannula 312 accommodates the delivery of medication fluid to the patient; a self-sealing septum 314 coupled to the base structure 306 and configured to fluidly seal the upstream end of the cannula 312; a body-insertable physiological analyte sensor 316 coupled to the base structure 306, wherein the sensor 316 facilitates the measurement of a physiological characteristic of the patient (such as blood glucose); and an electronics assembly 318 coupled to the base structure 306 and implemented on the circuit board 310. The electronics assembly 318 is schematically depicted in FIG. 10, and various unlabeled electronic components and devices of the electronics assembly 318 are shown in FIGS. 9, 11, 12, 14, 19, and 20.

The base structure 306 may include a rigid housing or platform 320 that is designed and configured to support the various components of the base unit 302. The platform 320 may, for example, be fabricated from a molded or machined plastic material or any appropriate material. The circuit board 310 is mounted to the platform 320, which also includes structural features for mounting and securing the cannula 312, the septum 314, the sensor 316, etc. As shown in FIG. 14 and FIG. 19, the septum 314 is maintained in position between the base structure 306 and the lid assembly 308 such that it can seal the upstream end of the cannula 312 when the top cover assembly 304 is removed from the base unit 302. The top end of the septum 314 is accessible via a hole 322 formed in the top surface 324 of the lid assembly 308 (which corresponds to the top surface of the base unit 302). Also shown in FIG. 14 and FIG. 19 is another septum 326 that seals another hole 328 formed in the top surface 324. As explained in more detail below, the septum 326 seals the hole 328 after insertion of the sensor 316.

Referring to the block diagram of FIG. 10, the base structure 306 includes the following items, without limitation: the electronics assembly 318; a film connector 332 electrically coupled to the sensor leads of the sensor 316; an interconnect structure 334; conductive pads 336 arranged and configured to contact corresponding interconnection plugs of the lid assembly 308; and at least one battery 338 (or other type of power supply). The film connector 332 is also shown in FIG. 11 and FIG. 12. The conductive pads 336 are also shown in FIG. 20 (in a cross-sectional view). In practice, the electronics assembly 318 is coupled to the base structure 306 (by way of the circuit board 310), and the electronics assembly 318 is electrically connected to the sensor leads to obtain measurements of the physiological characteristic in an analog domain. The electronics assembly 318 includes a digital processing circuit and/or suitable digital processing logic to convert measurements of the physiological characteristic from the analog domain into digital sensor data, to digitally process the digital sensor data into conditioned digital sensor data, and to communicate the conditioned digital sensor data to the fluid infusion device 102, which is associated with or connected to the infusion-sensor unit 112. In accordance with certain embodiments, the electronics assembly 318 includes at least the following items, without limitation: a small rechargeable battery that supports data collection and sensor power during brief periods when the top cover assembly is disconnected; a memory device, chip, or element that stores measurement data (which may be collected during disconnect periods) for later data retrieval; sensor analog front end discrete components with the possibility of supporting an electro impedance spectroscopy diagnostic and/or other forms of sensor diagnostics; a low power microprocessor device that is responsible for the required processing intelligence and logic (e.g., data communication, commanding the analog front end circuit, digital data processing).

Referring to FIG. 10, FIG. 11, and FIG. 12, the exemplary glucose sensor embodiment presented here employs a sensor 316 having three sensor leads 344. The sensor leads 344 include a reference conductor for a reference electrode of the sensor 316, a working conductor for a working electrode of the sensor 316, and a counter conductor for a counter electrode of the sensor 316. The sensor leads 344 provide analog signal values to the electronics assembly 318, by way of the film connector 332 and the interconnect structure 334, which can be realized with conductive traces, lines, or elements of the circuit board 310. In this regard, FIG. 12 depicts an exemplary implementation that includes a piece of adhesive 345 for affixing the end of the sensor 316 to the circuit board 310, and that includes conductive traces 346 or pads that form a part of the interconnect structure 334. The film connector 332 electrically couples the sensor leads 344 to the conductive traces 346, which in turn are electrically coupled to the electronics assembly 318, the battery 338, and the conductive pads 336 (refer to FIG. 10).

The illustrated embodiment has three conductive pads 336, which are assigned to a power conductor, a ground conductor, and a data conductor for communication of conditioned digital sensor data from the electronics assembly 318 to the fluid infusion device 102. These conductive pads 336 are also utilized to provide operating power from the fluid infusion device 102 to the electronics assembly 318 when the top cover assembly 304 is coupled to the base unit 302. The battery 338 provides "backup" operating power to the electronics assembly 318 when the top cover assembly 304 is removed from the base unit 302.

The lid assembly 308 of the base unit 302 will now be described with particular reference to FIGS. 9 and 13-20. The lid assembly 308 may, for example, be fabricated from a molded or machined plastic material or any appropriate material, as a unitary one-piece construction or as an assembly of different parts. As mentioned above, the illustrated embodiment of the lid assembly 308 includes the top surface 324 and the holes 322, 328 that extend to the top surface 324. The illustrated embodiment of the lid assembly 308 also includes a suitably configured connector structure 350 that is used to convey the digital data generated by the base unit 302, and to provide operating voltage to the base unit 302 from the host fluid infusion device.

The illustrated embodiment of the connector structure 350 includes a pedestal 352 extending from the base unit 302 and interconnection plugs 354 positioned within the pedestal 352. The pedestal 352 can be integrally formed with the remaining material of the lid assembly 308. The interconnection plugs 354 are electrically conductive elements that establish electrical connections between the electronics of the base unit 302 and corresponding electrical contacts of the top cover assembly 304 (when the top cover assembly 304 is attached to the base unit 302). For this particular embodiment, the interconnection plugs 354 are formed from a conductive elastomeric material, which is desirable to establish good and reliable electrical contacts. The pedestal 352 includes through holes formed therein to receive and retain the interconnection plugs 354.

The lower ends of the interconnection plugs 354 are electrically coupled to the corresponding conductive pads 336 of the electronics assembly 318 in the base unit 302 (as mentioned previously; see FIG. 20). When the top cover assembly 304 is coupled to the base unit 302, the upper ends of the interconnection plugs 354 mate with, and physically contact, corresponding electrical contact pads of an electrical interconnect assembly mounted inside the top cover assembly 304 (as described in more detail below). Thus, the interconnection plugs 354 are designed to physically and electrically couple the conductive pads 336 to the electrical interconnect assembly of the top cover assembly 304. As mentioned above, the interconnection plugs 354 correspond to a power conductor, a ground conductor, and a data conductor for communication of the conditioned digital sensor data.

Referring to FIG. 16, the medical device component 100 may also include a protective cap 358 for the connector structure 350. The protective cap 358 is shaped, sized, and configured to mate with and seal the connector structure 350 when the top cover assembly 304 is removed from the base unit 302. The protective cap 358 prevents electrical shorting of the interconnection plugs 354 and minimizes contamination and damage to the connector structure 350.

The top cover assembly 304 will now be described with particular reference to FIGS. 9 and 17-20. The top cover assembly 304 is designed and configured to be installed onto and removed from the base unit 302 as needed. In certain embodiments, the top cover assembly 304 and the base unit 302 are cooperatively and compatibly designed with certain features to enable the top cover assembly 304 to be secured onto the base unit 302. During normal operation of the infusion system, the top cover assembly 304 is affixed to the base unit 302 to establish and maintain both fluid connections and electrical connections between the top cover assembly 304 and the base unit 302. As explained previously, an infusion tube provides the fluid and electrical connections between the top cover assembly 304 and the attached fluid infusion device. The patient or a caregiver can temporarily remove the top cover assembly 304 from the base unit 302 for various reasons, e.g., bathing, showering, swimming, replacement of the infusion set, maintenance of the infusion set or the infusion device, cleaning, or the like.

The top cover assembly 304 generally includes, without limitation: a lid structure 360; an infusion tube 362 (which carries the sensor conductors or has the sensor conductors integrated therein, as described above); a tubing connector 364; and an electrical interconnect assembly 366. These primary elements will be described in more detail below.

The lid structure 360 may, for example, be fabricated from a molded or machined plastic material or any appropriate material, as a unitary one-piece construction or as an assembly of different parts. For this particular embodiment, the lid structure 360 is designed and configured to releasably mate with the base structure 306 of the base unit 302. To this end, the lid structure 360 and the base structure 306 can include snap-fitting features, clips, tabs, buttons, dimensions to accommodate a press-fit or pressure-fit engagement, slots and keys, etc. In this regard, FIG. 17 and FIG. 19 depict two tabs 368 of the lid structure 360 that engage and cooperate with corresponding slots, tabs, or shoulders of the base structure 306. The lid structure 360 resembles a shell having an interior space 370 that is defined by an inner surface 372 of the lid structure 360 (see FIG. 17).

The infusion tube 362 represents one exemplary embodiment of the infusion tube 110 described above. The infusion tube 362 is coupled to (or near) the inner surface 372 of the lid structure 360 such that an end of the tube 362 terminates within the interior space 370. For the illustrated embodiment, the lid structure 360 includes at least one structural feature 376 that receives, secures, and retains the end of the tube 362. FIG. 18 depicts the structural feature 376 in cross-section, i.e., with a portion of it removed. As shown in FIG. 17 and FIG. 18, the end of the infusion tube 362 is exposed to allow the sensor conductors 378 to extend from the infusion tube 362. Accordingly, the sensor conductors 378 terminate within the interior space 370 of the lid structure 360. Thus, the terminating end of each sensor conductor 378 extends from the end of the infusion tube 362 and is exposed for connection to the electrical interconnect assembly 366.

The tubing connector 364 is shown in FIGS. 17-19. The tubing connector 364 is fluidly coupled to the infusion tube 362 such that it diverts the fluid flow path from inside the infusion tube 362. For this particular embodiment, the downstream end 380 of the tubing connector 364 resides inside the infusion tube 362 and forms a seal with the interior surface of the infusion tube 362 to inhibit leakage of fluid around the outer surface of the tubing connector 364. In this regard, the tubing connector 364 is preferably fabricated from a rigid material (e.g., hard plastic or stainless steel) that can be press fit inside the infusion tube 362. As shown in FIG. 18, the tubing connector 364 can be introduced into the infusion tube 362 through a slot 382 or other opening in the wall of the infusion tube 362.

The distal (downstream) end 384 of the tubing connector 364 is supported by the structural feature 376 of the lid structure 360 (see FIG. 17). The distal end 384 of the tubing connector 364 is rigid and somewhat pointed such that it can easily penetrate the self-sealing septum 314 of the base structure 306 to establish a fluid delivery flow path from inside the infusion tube 362 to the cannula 312 when the top cover assembly 304 is coupled to the base unit 302 (see FIG. 19). Thus, when the top cover assembly 304 is properly installed onto the base unit 302, the tubing connector directs flow of the medication fluid from inside the infusion tube 362, through the septum 314, and into the cannula 312, which in turn delivers the medication fluid to the body of the patient.

The electrical interconnect assembly 366 of the top cover assembly 304 is best shown in FIG. 17 and FIG. 18. A portion of the electrical interconnect assembly 366 is also shown in the cross-sectional views of FIG. 19 and FIG. 20. The interconnect assembly 366 can be implemented as a printed circuit board that is fabricated using known techniques and methodologies. The interconnect assembly 366 is physically coupled to the inner surface 372 of the lid structure 360 in the desired location. For this particular embodiment, the interconnect assembly 366 is a passive component having electrically conductive traces, plugs, contact pads, and/or other elements that are arranged to electrically connect the sensor conductors 378 to the interconnection plugs 354 of the base unit 302. Accordingly, when the top cover assembly 304 is coupled to the base unit 302, the electrical interconnect assembly 366 establishes electrical connectivity between the sensor conductors 378 and the electronics assembly 318 of the base unit 302, which facilitates communication of the conditioned digital sensor data from the electronics assembly 318 to the fluid infusion device. In addition, the electrical interconnect assembly 366 allows the fluid infusion device to provide operating power (voltage) to the base unit 302 as needed.

As shown in FIG. 17 and FIG. 18, the sensor conductors 378 can be bonded, soldered, press-fit, force-fit, or otherwise coupled to corresponding contacts formed on an exposed surface 390 of the interconnect assembly 366. The interconnect assembly 366 includes three electrical contact pads 392—one for each of the sensor conductors 378. The interconnect assembly 366 also includes three conductive paths (hidden from view) that connect the contact pads 392 to the contacts assigned to the respective sensor conductors 378. The shape, size, layout, and arrangement of the contact pads 392 are compatible with the arrangement of interconnection plugs 354 (see FIG. 20). When the top cover assembly 304 is installed on the base unit 302, the contact pads 392 are forced into physical and electrical contact with the upper ends of the interconnection plugs 354.

Referring again to FIGS. 9, 13, 14, and 16-19, the hole 322 formed in the top surface 324 of the base unit 302 accommodates insertion and withdrawal of the tubing connector 364 (during installation and removal of the top cover assembly 304), and also accommodates an insertion needle used to insert the cannula 312 into the skin of the patient when the base unit 302 is initially deployed. FIG. 14 shows the base unit 302 without the tubing connector 364, and FIG. 19 shows the base unit 302 with the tubing connector 364 installed through the hole 322 and into the septum 314. The other hole 328 formed in the top surface 324 of the base unit 302 accommodates another insertion needle that is used to insert the physiological analyte sensor 316 into the skin of the patient when the base unit 302 is initially deployed. After the base unit 302 has been deployed, the hole 324 remains plugged by the septum 326.

Alternative Connection Schemes

Figure 21:
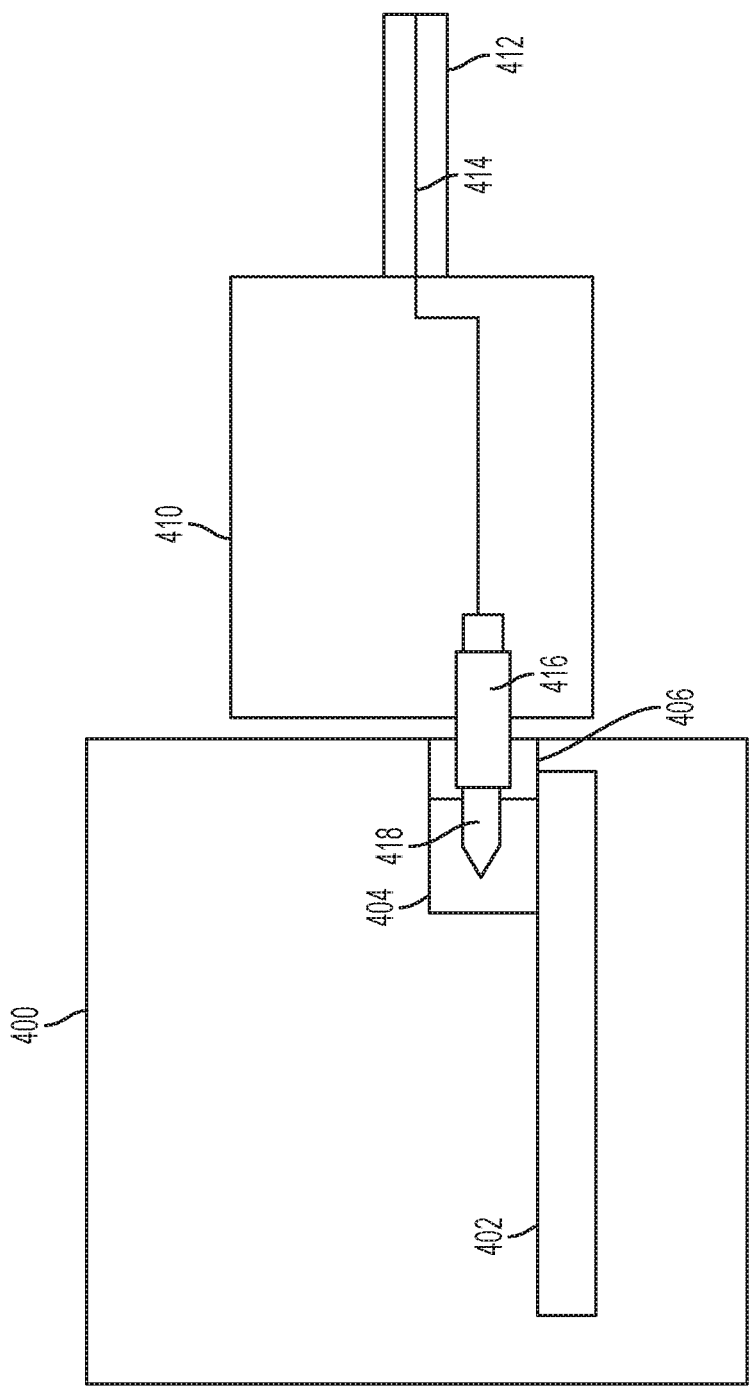
FIG. 21 is a simplified block diagram schematic of an alternative connection scheme suitable for use with a combined sensor-infusion unit.

The exemplary embodiment described above utilizes the top cover assembly 304 as a mechanism for establishing the fluid and electrical connections to the base unit 302. In practice, any suitably configured connection methodology or scheme can be employed with a combined sensor-infusion unit of the type described herein. In this regard, FIG. 21 is a simplified block diagram schematic of an alternative connection scheme suitable for use with a combined sensor-infusion unit 400 of the type generally described above. This description assumes that the sensor-infusion unit 400 includes a sensor electronics assembly 402, an interconnect 404 formed of an electrically conductive elastomer, and a self-sealing septum 406. The interconnect 404 is electrically coupled to one or more contact pads of the sensor electronics assembly 402.

The sensor-infusion unit 400 is compatible with a base connector 410, which is attached to an infusion tube 412 having embedded or integrated sensor conductors 414 (depicted as a single line in FIG. 21). For simplicity and ease of illustration, FIG. 21 does not show the fluid flow path for the medication fluid carried by the infusion tube 412. Nonetheless, it should be appreciated that the medication fluid is delivered to the patient via the infusion tube 412, through a fluid conduit or path formed in the base connector 410, and through a corresponding fluid conduit or path formed in the sensor-infusion unit 400.

The sensor conductors 414 are electrically coupled to the sensor-infusion unit 400 by way of an electrical connector 416, which includes connection pins 418 for the sensor conductors 414. FIG. 21 only shows one connection pin 418, which penetrates the septum 406 to establish an electrical contact with the interconnect 404 (as shown in FIG. 21). The electrical connection between the base connector 410 and the sensor-infusion unit 400 is waterproof (or water resistant by at least a specified amount). The septum 406 is self-sealing to create a watertight seal when the base connector 410 is removed from the sensor-infusion unit 400.

The manner in which the sensor conductors 414 are terminated from the infusion tube 412 to the base connector 410 can vary from one embodiment to another. In this regard, any of the following techniques can be leveraged, without limitation: soldering wires to a circuit board or a conductive pin; mechanical pin connections; hot bar bonding or soldering wires to solder pads of a circuit board; connecting wires to a conductive elastomer; pressing or forcing wires into a cutter element to make electrical connections; forcing a cutter element into the infusion tube 412 to make electrical connections with the sensor conductors 414; etc.

Figure 22:
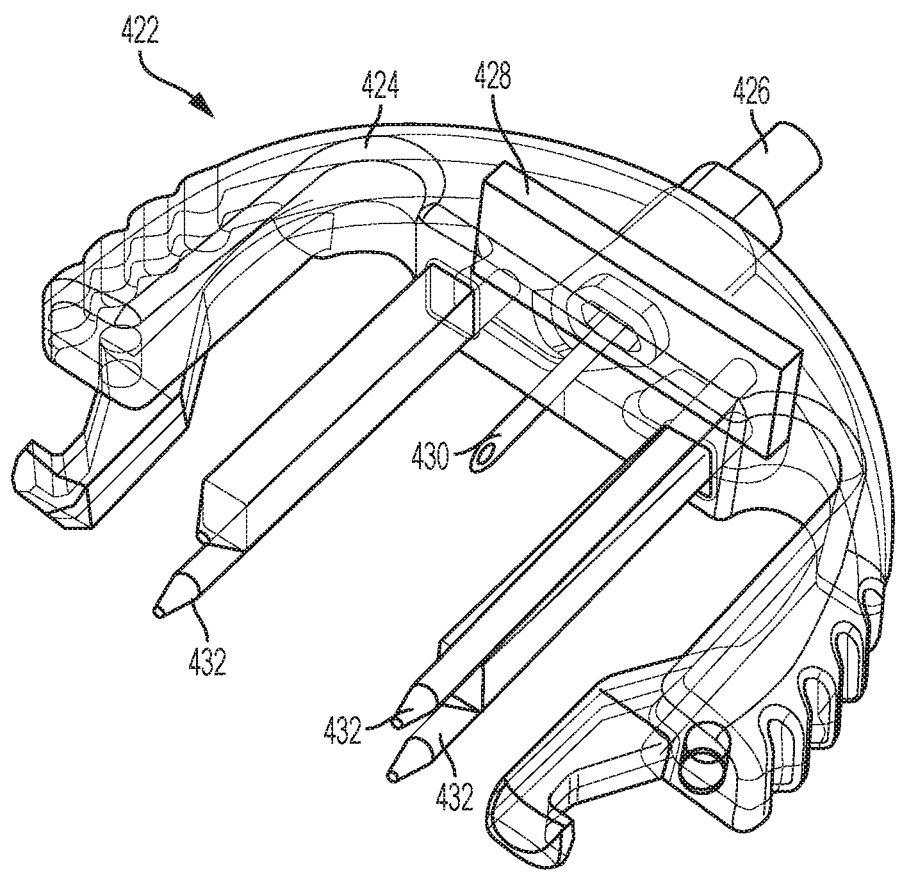
FIG. 22 is a partially phantom perspective view of an exemplary embodiment of a base connector that provides both fluid and electrical connections to a combined sensor-infusion unit.

FIG. 22 is a partially phantom perspective view of an exemplary embodiment of a base connector 422 that provides both fluid and electrical connections to a combined sensor-infusion unit (not shown). The depicted base connector 422 leverages a legacy configuration that is compatible with currently available glucose sensor packages. The legacy configuration has been modified to enable the base connector 422 to establish the required number of electrical connections (e.g., three for the exemplary embodiment presented here). The base connector 422 includes a generally c-shaped body 424 that is designed to mechanically attach to the sensor-infusion unit. The body 424 is configured to receive an infusion tube 426 that carries three sensor conductors (partially obscured from view in FIG. 22). The base connector 422 also includes an interface component 428 that serves as a fluid transition from the infusion tube 426 to an infusion needle 430, and as an electrical transition from the sensor conductors to three corresponding connector pins 432. The infusion needle 430 and the connector pins 432 mate with, and couple to, respective elements of the sensor-infusion unit.

Figure 23:
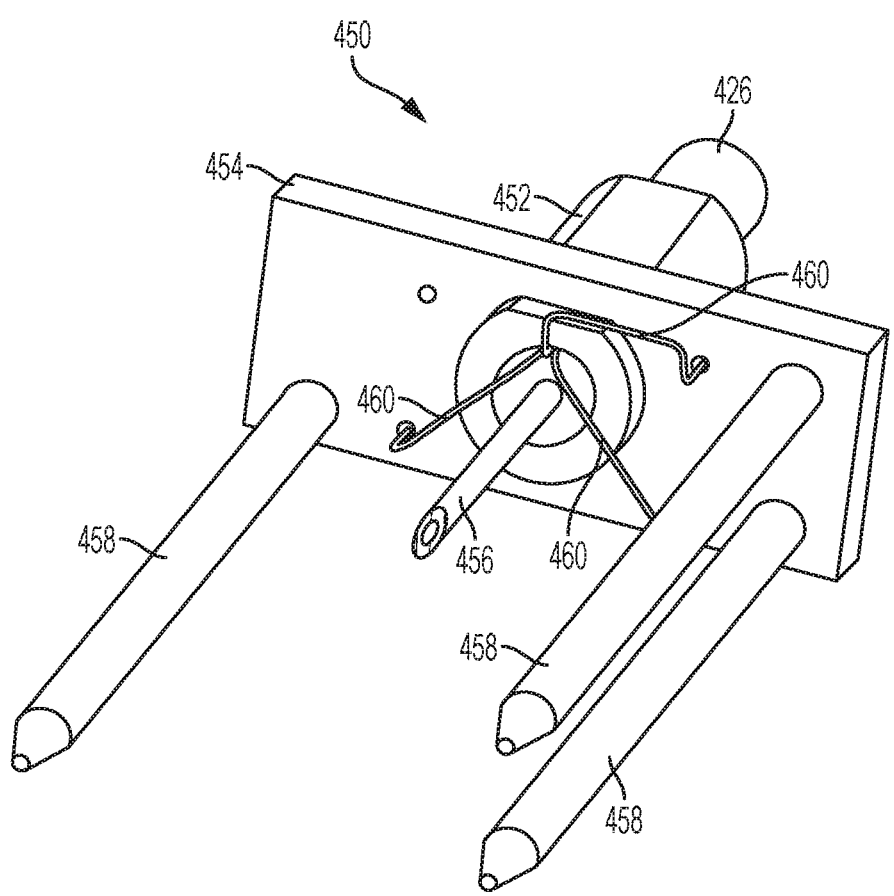
FIGS. 23-29 are perspective views of various fluid/electrical connection structures suitable for use with a base connector of the type shown in FIG. 22.

FIG. 23 is a perspective view of a fluid/electrical connection structure 450 suitable for use with the base connector 422. The connection structure 450 includes a coupling element 452 that couples the infusion tube 426 to an interface component 454, which can be implemented as a printed circuit board. An infusion needle 456 protrudes from a seal, plug, or septum in the front of the interface component 454. Three connector pins 458 extend from the front of the interface component 454. The three sensor conductors 460 also extend from the seal, plug, or septum, and each conductor 460 is soldered, welded, or otherwise electrically connected to a respective electrical junction point on the interface component 454. Each electrical junction point is connected to one of the connector pins 458.

Figure 24:
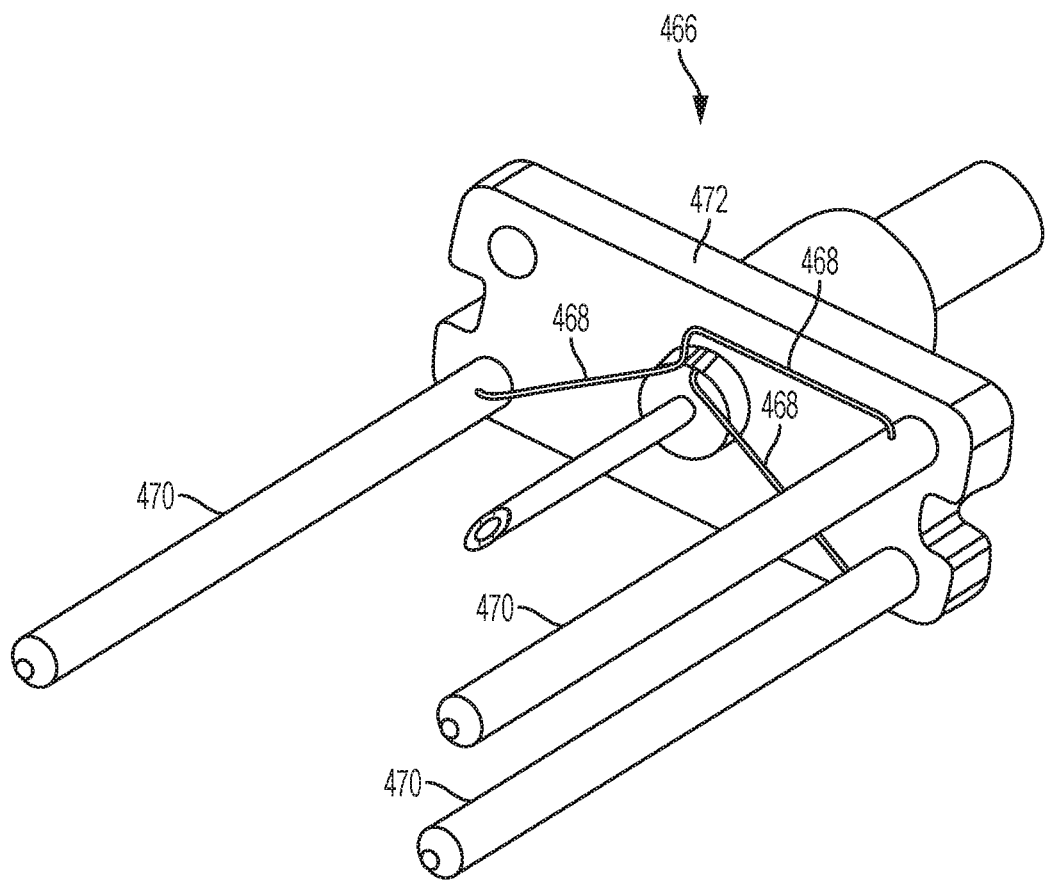

FIG. 24 is a perspective view of another fluid/electrical connection structure 466 that is suitable for use with the base connector 422. The connection structure 466 is similar to the connection structure 450 shown in FIG. 23, and similar or identical features and elements will not be redundantly described here. In contrast to that described above for the connection structure 450, the sensor conductors 468 of the connection structure 466 are attached directly to the connector pins 470 (rather than to the interface component 472). For this arrangement, the interface component 472 is fabricated from a nonconductive material, such as plastic.

Figure 25:
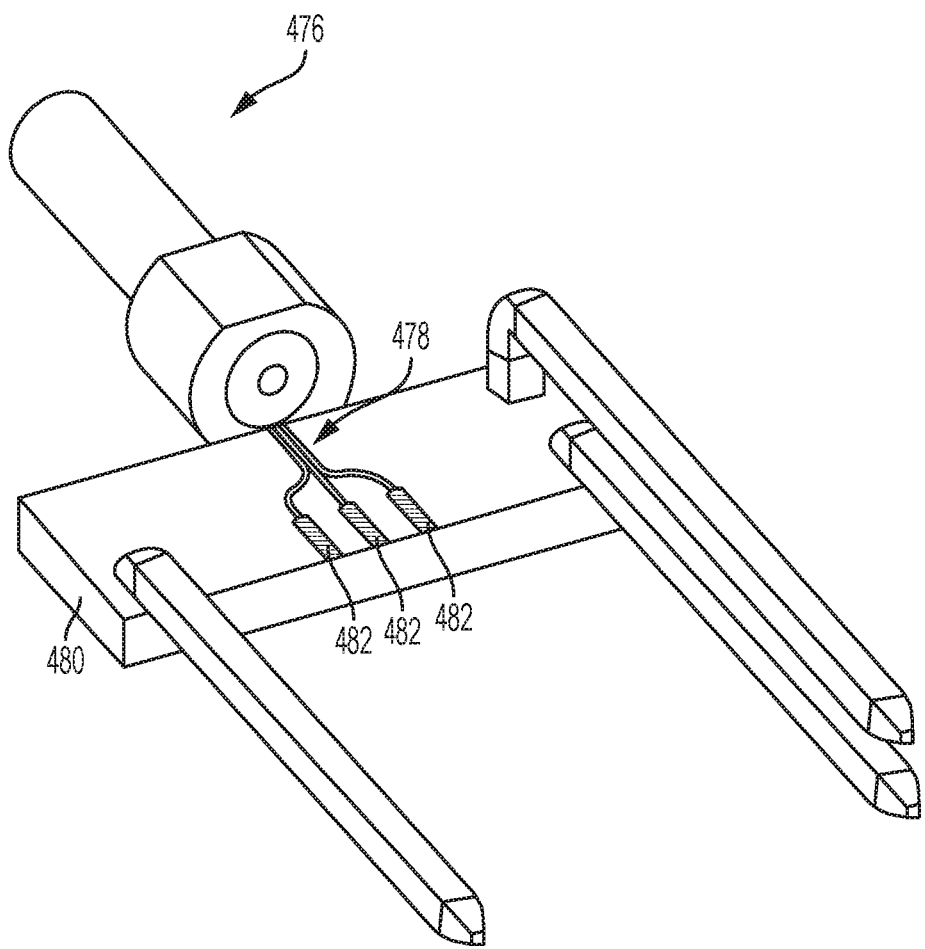

FIG. 25 is a perspective view of another fluid/electrical connection structure 476 that is suitable for use with the base connector 422. The connection structure 476 is similar to the connection structure 450 shown in FIG. 23, and similar or identical features and elements will not be redundantly described here. For this embodiment, the sensor conductors 478 extend from the infusion tube in alignment with the interface component 480, and are bonded to conductive pads 482 by traditional soldering or hot bar soldering for ease of manufacturing.

Figure 26:
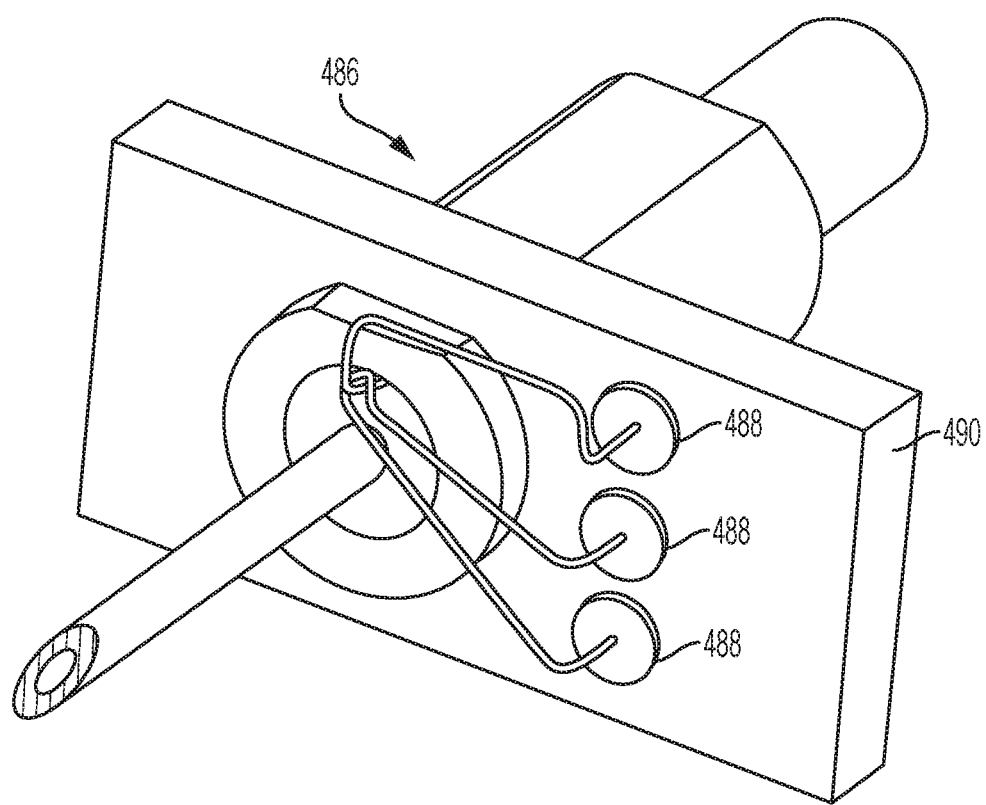

FIG. 26 is a perspective view of another fluid/electrical connection structure 486 that is suitable for use with the base connector 422. The connection structure 486 is similar to the other connection structures mentioned previously, and similar or identical features and elements will not be redundantly described here. For this embodiment, the sensor conductors extend from the infusion tube and are terminated in conductive elastomer plugs 488 located in the interface component 490. The conductive elastomer plugs 488 are connected to an interconnect or circuit arrangement of the interface component 490 (not shown in FIG. 26), which in turn is electrically coupled to certain features of the sensor-infusion unit.

Figure 27:
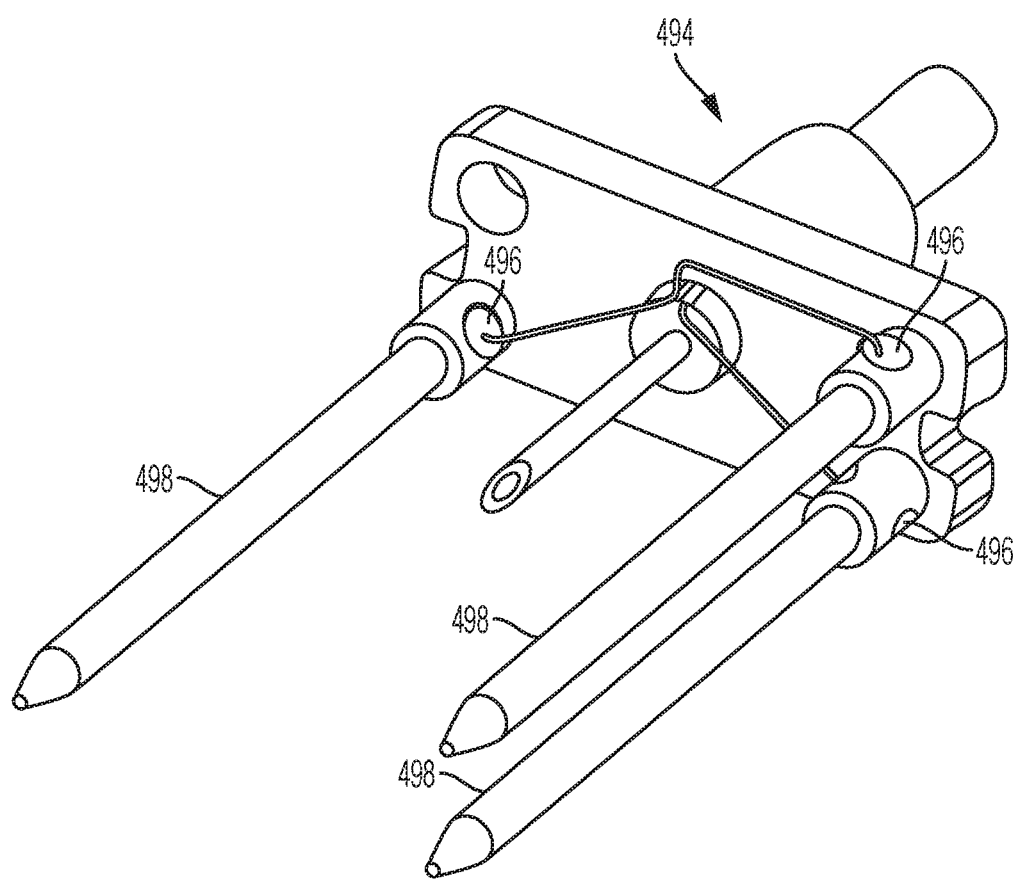

FIG. 27 is a perspective view of another fluid/electrical connection structure 494 that is suitable for use with the base connector 422. The connection structure 494 is similar to the other connection structures mentioned previously, and similar or identical features and elements will not be redundantly described here. For this embodiment, the sensor conductors extend from the infusion tube and are terminated in conductive elastomer plugs 496 located in holes formed in the connector pins 498.

Figure 28:
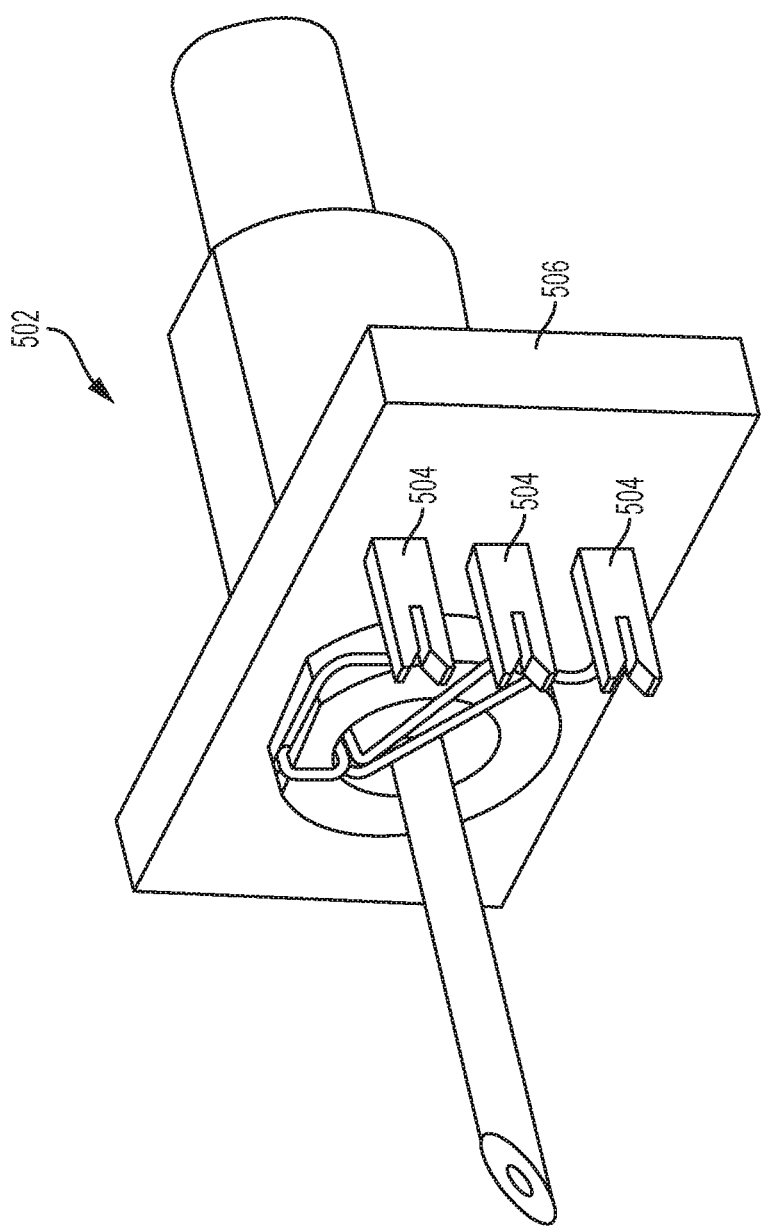

FIG. 28 is a perspective view of another fluid/electrical connection structure 502 that is suitable for use with the base connector 422. The connection structure 502 is similar to the other connection structures mentioned previously, and similar or identical features and elements will not be redundantly described here. For this embodiment, each sensor conductor extends from the infusion tube and is pressed into a conductive cutter block 504 that extends from the interface component 506. The cutter blocks 504 are connected to an interconnect or circuit arrangement of the interface component 506 (not shown in FIG. 26), which in turn is electrically coupled to certain features of the sensor-infusion unit.

Figure 29:
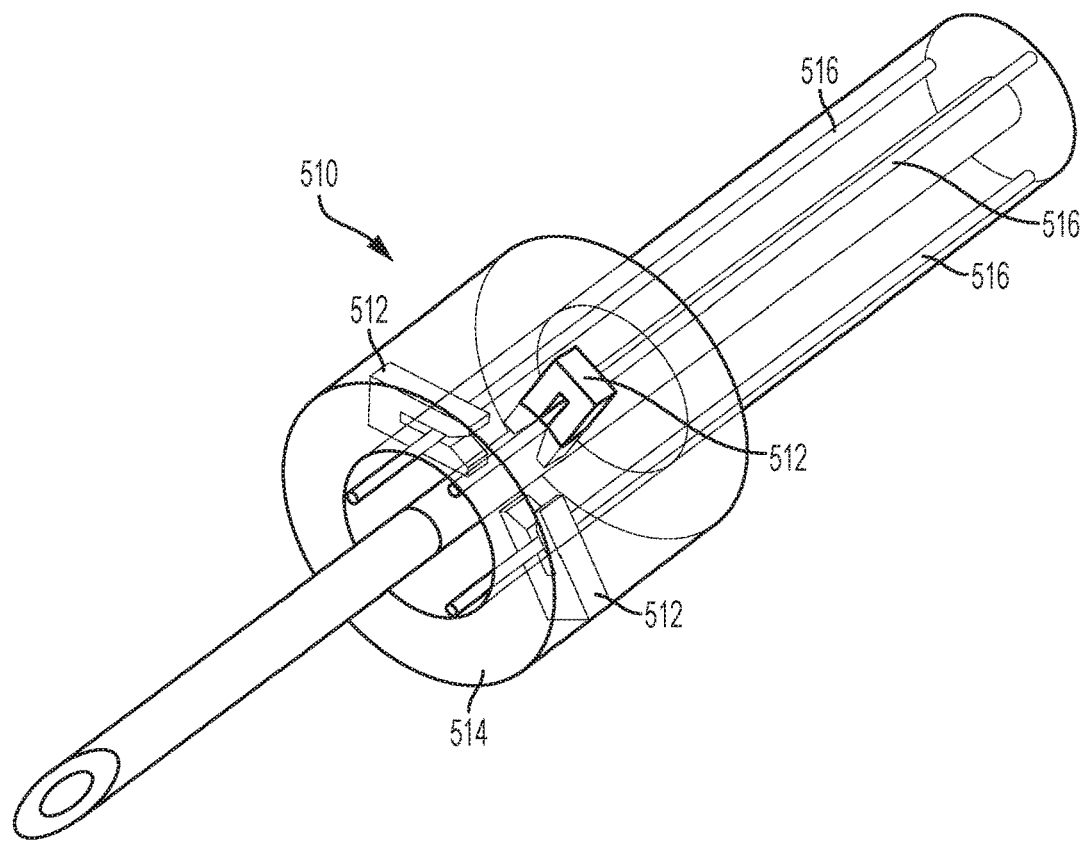
Figure 30:
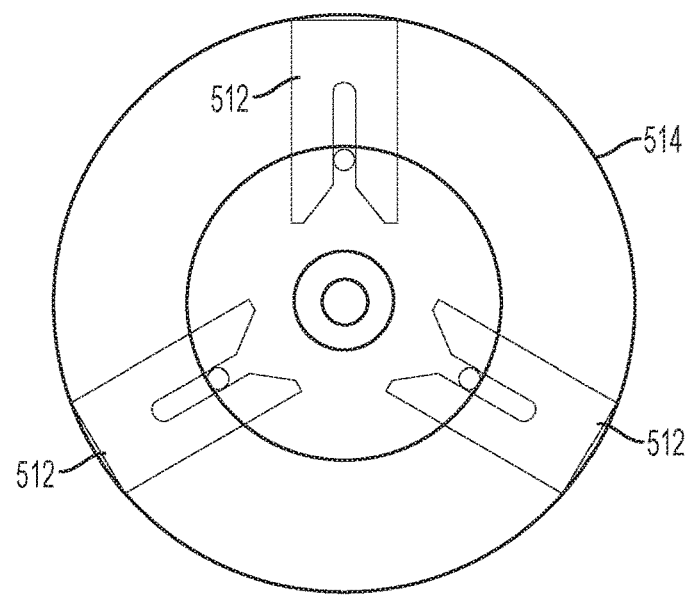
FIG. 30 is a partially phantom end view of a portion of the connection structure depicted in FIG. 29.

FIG. 29 is a perspective view of another fluid/electrical connection structure 510 that is suitable for use with the base connector 422. The connection structure 510 employs three conductive cutter blocks 512 that cut into the infusion tube 514 to make the electrical connections to the sensor conductors 516 (located inside the infusion tube 514). The cutter blocks 512 are connected to an interconnect or circuit arrangement, or to external wires that can be routed to the sensor-infusion unit. FIG. 30 is a partially phantom end view of a portion of the connection structure 510, showing how the cutter blocks 512 enter the infusion tube 514 to make the connections with the sensor conductors 516.

Modular Embodiment

The embodiments described above include a one-piece combined sensor-infusion unit that includes both the sensor element and the fluid infusion element packaged together. Such an integrated implementation is desirable and appropriate when the expected useful lifespan of the sensor element is approximately the same as the expected useful lifespan of the infusion element (e.g., three days, five days, one week). At the time of this writing, continuous glucose sensors typically have a longer useful lifespan than insulin infusion sets. Consequently, a combined sensor-infusion unit that leverages existing glucose sensor and insulin infusion technology may have a useful lifespan that is limited by the specifications of the insulin infusion technology. To address this scenario, alternative embodiments of a combined sensor-infusion unit utilize a modular design having physically distinct sensor and infusion modules. The modular implementation is described in more detail below with reference to FIG. 31 and FIG. 32.

Figure 31:
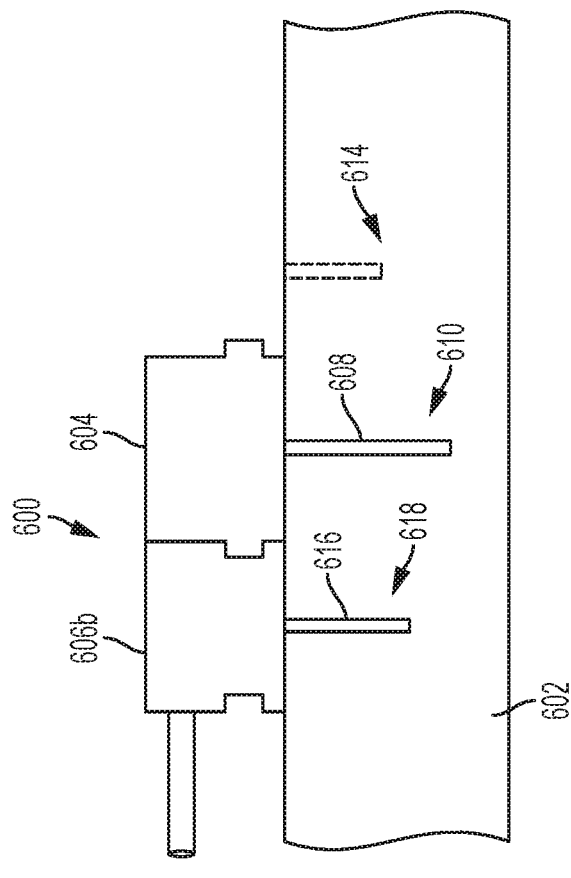
FIG. 31 is a schematic representation of an exemplary embodiment of a modular sensor-infusion unit.
Figure 31:
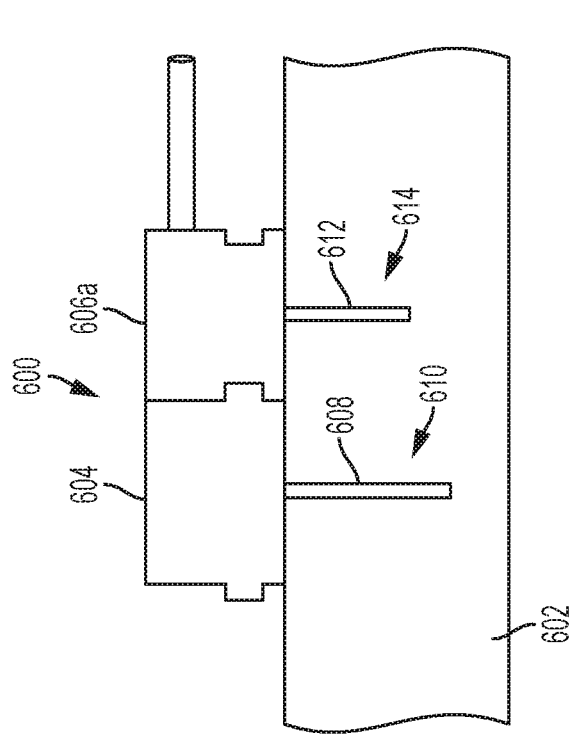

FIG. 31 is a schematic representation of an exemplary embodiment of a modular sensor-infusion unit 600. The left side of FIG. 31 depicts the modular sensor-infusion unit 600 deployed on the skin 602 of the patient during an initial period of time (e.g., the first three days of use), and the right side of FIG. 31 depicts the modular sensor-infusion unit 600 deployed on the skin 602 during a subsequent period of time (e.g., the last three days of use). The unit 600 includes a sensor module 604 and a compatible infusion module 606. The two modules 604, 606 can be removably coupled together. This example assumes that the sensor module 604 has a useful lifespan rating of six days, and that each infusion module 606 has a useful lifespan rating of three days. Accordingly, a first infusion module 606a is used for the first three days, and a second infusion module 606b is used for the final three days.

The sensor module 604 includes a sensor element 608 intended for insertion at a sensor site 610 of the patient. The infusion module 606a includes a cannula 612 intended for insertion at a first infusion site 614 of the patient. The infusion module 606b includes a cannula 616 intended for insertion at a second infusion site 618 of the patient, wherein the second infusion site 618 is different than, and remote from, the first infusion site 614. The initial infusion module 606a is replaced with the second infusion module 606b after three days of use. As depicted in FIG. 31, the first infusion site 614 is left to heal/recover after removal of the first infusion module 606a.

The modular design allows either the sensor module 604 or the infusion module 606 to by replaced during wear. The sensor and infusion modules connect together to form a single on-body assembly. This configuration enables sensors with longer wearable lifespan to be used with infusion sets with shorter wearable time, and provides the versatility to replace one of the modules only as needed, which in turn reduces the cost burden.

The modular design builds on the integrated implementation described above, where the sensor electronics assembly is integrated into the combined unit and has a tethered connection to the infusion device through embedded wires in the infusion set tubing. For this modular implementation, the sensor electronics can reside in the sensor module, the infusion module, or both. Each module may contain connection points on each side of the module to allow site rotation.

FIG. 31 depicts an exemplary use case for a six-day wear sensor and three-day wear infusion sets. On the first day, the sensor and infusion modules are deployed (inserted) together. On the fourth day, the first infusion module 606a is removed and the second infusion module 606b is inserted at the opposite side from the previous site, and connected to the sensor module 604.

The modular design accommodates extended wear times. At the time of this writing, the technology for long-term continuous glucose sensors is advancing quicker than that for insulin infusion sets. Accordingly, this modular design makes a 14-day combined unit possible. For example: a six-day sensor can be connected with two three-day infusion sets; a 14-day sensor can be connected with two seven-day infusion sets; and a 12-day sensor can be connected to four 3-day infusion sets.

Sterilization

Sensor and infusion set modules can be sterilized separately based on their sterilization compatibility. This reduces the burden of developing a single sterilization platform. In this regard, current sensor technology is compatible with e-beam sterilization, and infusion sets are compatible with ethylene oxide sterilization. Sensor electronics or components that are incompatible with e-beam sterilization can reside in the infusion set module for sterilization using ethylene oxide.

Replacement

If either the sensor or infusion set module malfunctions or otherwise requires maintenance during wear, only the affect module needs to be replaced without replacing the entire combined assembly.

Interchangeability

Various models of sensors and infusion sets can be connected together. For example: either a 6 mm or 9 mm cannula infusion set module can be connected with the sensor module; different sensor generations can be connected to the infusion set module; and upgrades for either the sensor or infusion set module would have minimal impact on the other module, due to the use of a standardized connection.

Insertion/Deployment

In order to simplify replacement of the modules, an insertion device can be designed to explant and insert new modules as needed. An exemplary use case and workflow may be as follows:

Step 1: Load new a sensor or infusion set module into the insertion device.

Step 2: Align the insertion device overlying the currently deployed modular assembly.

Step 3: Operate the insertion device to explant the module that is to be replaced.

Step 4: Operate the insertion device to insert and attach the new module onto the remaining assembly.

Figure 32:
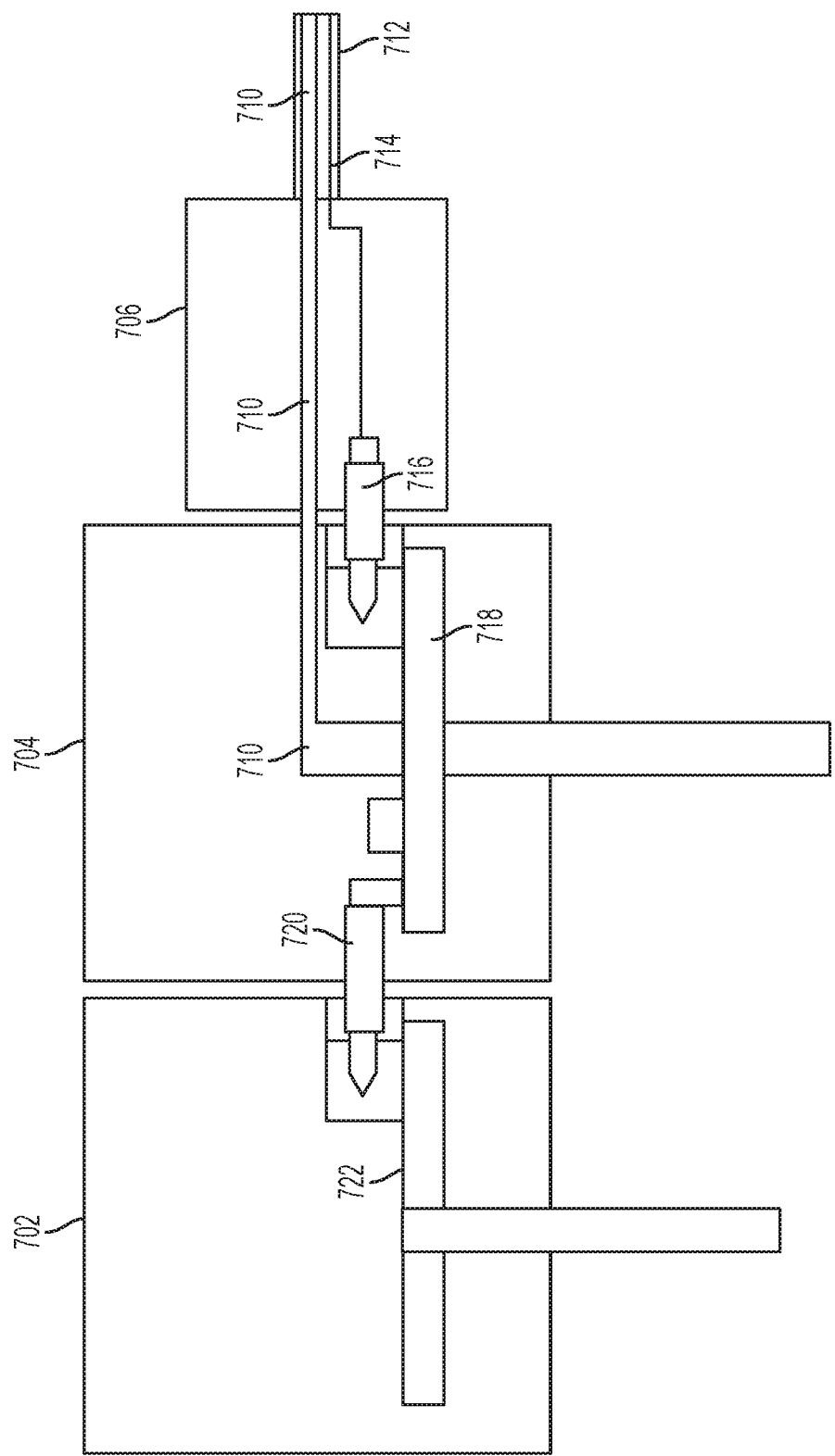
FIG. 32 is a simplified block diagram of a connection scheme suitable for use with a modular sensor-infusion unit.

FIG. 32 is a simplified block diagram of a connection scheme suitable for use with a modular sensor-infusion unit of the type described above with reference to FIG. 31. The exemplary embodiment depicted in FIG. 32 includes a sensor module 702, an infusion module 704, and a connector 706. Some elements, features, and functionality of the modular sensor-infusion unit shown in FIG. 32 are similar or identical to those described above with reference to FIG. 21. Accordingly, similar and identical items will not be redundantly described here.

The illustrated embodiment has the sensor module 702 as the "last in line" component, the infusion module 704 as the "first in line" component, and the connector 706 coupled to the infusion module 704 to provide the medication fluid and the operating voltage/power to the infusion module 704. In other embodiments, the positions of the sensor module 702 and the infusion module 704 can be swapped (with necessary modifications to the fluid and/or electrical flow paths). A fluid flow path 710, which leads to the infusion site of the patient, is defined within at least the following components: an infusion tube 712; the connector 706; and the infusion module 704. An electrically conductive path (which may include any number of conductors, wires, traces, contact pads, or the like), which establishes connectivity between the host fluid infusion device and the modular sensor-infusion unit, includes or is defined by at least the following components: sensor conductors 714 carried by or integrated with the infusion tube 712; a first electrical connector 716; an electronics assembly 718 of the infusion module 704; a second electrical connector 720; and an electronics assembly 722 of the sensor module 702. The connectors 716, 720 are similar to the electrical connector 416 described above, and the electronics assembly 718, 722 are similar to the electronics assembly 402 described above (see FIG. 21).

The electronics assembly 718 of the infusion module 704 need not include any active components. In certain embodiments, the electronics assembly 718 serves as a pass-through component that only contains conductive traces, wires, contact pads, and the like, to electrically couple the sensor module 702 to the connector 706. In other embodiments, the electronics assembly 718 may include some or all of the electronics required to perform analog-to-digital conversion, digital data conditioning and processing, data transmission, power regulation, etc.

Summary/Conclusions

The one-piece combined and miniaturized sensor-infusion unit described above has an infusion set with an electronic connection to the host infusion device. The infusion set eliminates the need for a sensor transmitter, thus significantly reducing the on-body footprint. Electrical signals are routed in or along the infusion set tubing to allow for power and data transmission, eliminating the need for a large battery and radio frequency circuitry at the sensor base.

A practical goal that is achieved by the combined sensor-infusion unit is to provide an extended wear infusion set (up to seven days, for example) having a reduced on-body footprint. As an alternate embodiment, a two-part modular sensor-infusion unit has also been presented here. In accordance with one example, the modular implementation can be used with a three-day insulin infusion module and a six-day glucose sensor module. The modular embodiment includes two detachable parts, one containing the glucose sensor with the integrated sensor electronics and the other being the infusion set. On day 1, the sensor and infusion set are deployed and inserted together. On day 4, the first infusion set is be removed and a new infusion set is inserted at the opposite side from the previous site and connected to the sensor module. Although the modular design requires more complex manufacturing consideration due to the complexity of inserting a second infusion set to the pre-existing sensor base on the body, there will still be a single on-body device. One practical goal of this alternative design is to maintain a relatively small form factor.

The disclosed embodiments are significantly smaller in size, and consume significantly less on-body area than existing products that a separately inserted glucose sensor and infusion catheter. Size reduction is achieved by distributing and integrating sensor electronics across the combined sensor-infusion unit and the host infusion device. Electrical wires can be embedded in the infusion set tubing to allow for power and data transmission between the combined sensor-infusion unit and the infusion device, thus eliminating the need for a large battery and wireless communication radio at the combined unit. Minimal electronics reside at the combined unit to power the sensor and condition the digital data before sending the data to the infusion device. With integrated electronics and wires embedded in the infusion tubing, the combined unit can be designed and marketed as a disposable device.

The combined sensor-infusion unit incorporates the infusion set cannula, glucose sensor, sensor electronics, and wired tubing connection. With the sensor electronics integrated into the combined unit, most of the elements of conventional wireless sensor transmitters can be eliminated to significantly reduce the device footprint. In this regard, the total on-body footprint of the one-piece sensor-infusion unit is approximately 50% less than separately inserted glucose sensor and insulin infusion catheters. For example, the on-body area of an exemplary embodiment is about 1.0 square inch.

A base assembly incorporates the infusion set cannula, glucose sensor, sensor electronics, and wired tubing connection. In order to connect infusion tube/wires with both a fluid path and electrical elements, a new connection design at the base is provided. The design of that connection provides a connection with a minimal overall size.

New glucose sensor and sensor electronics connection schemes can be utilized to minimize size and improve reliability.

An extended wear adhesive patch allows the combined sensor-infusion unit to be be adhered to the body for an extending period, such as seven days.

A waterproof design for the combined unit and tubing connection can be utilized to prevent damage to the sensor electronics.

A soft cannula can be used for medication delivery. In order to securely attach the cannula to the base assembly, a suitable cannula hub design can be leveraged.

The two-purpose connection between the tubing for insulin delivery and electrical elements should be robustly designed against strain, stress, and liquid leakage while minimizing the form factor and simplifying installation.

A single sterilization method for the glucose sensor, cannula, and sensor electronics can be based on ethylene oxide (EtO) or electron beam (e-beam) technology. Currently, EtO sterilization is used for infusion sets and e-beam sterilization for glucose sensors. In practice, an appropriate sterilization method should be chosen to results in the least design complexity.

An infusion set tubing with embedded wires as described herein supports data and power transmission between the base assembly and the infusion device. Conductive wires are placed along the entire length of the tubing. Various methods including co-extrusion processes can be used to integrate wires into the tubing. It is projected that the tubing material will maintain similar chemical properties (biocompatibility) to preserve insulin integrity. Wire terminations at the tubing ends will be developed for both the base assembly side and the infusion device side.

Signals from the combined sensor-infusion unit will be transmitted to the infusion device via the wired tubing, which will be connected at one end to the infusion device. A suitable connector and/or connection mechanism for the infusion device and tubing set enables reliable signal and power transmission between the components, via the wired tubing.

In certain embodiments, the wired connection to the infusion device is waterproof such that the system maintains its ingress protection rating (IPX8: 12 feet for 24 hours). The sensor-infusion unit can be implemented as a consumable device with a service life of about seven days, while the host infusion device has a design life of more than four years. The combination of the above-mentioned requirements provides for a carefully designed electrical connection to the infusion device. The connection must withstand four years of multiple connect/disconnect events, wear-and-tear including multiple drops, scratches, and exposure to water and various chemicals.

The sensor electronics at the base assembly and the infusion device are designed to support sensor function and signal transmission. Disposable hardware designs are considered to minimize component costs while supporting sensor diagnostics schemes and improvements in sensor reliability. The addition of a battery and memory to the base assembly enables the continued collection of sensor data in the event of a tubing disconnection during patient use. Electronics at the infusion device side includes hardware to power and communicate with the base assembly.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A medical device component for delivering medication fluid to a patient, the medical device component comprising:
 a body-mountable base unit comprising:
  a base structure;
  a lid assembly affixed and sealed to the base structure;
  a body-insertable cannula that accommodates delivery of medication fluid to the patient, the cannula having an upstream end securely attached to the base structure and having a downstream end extending from the base structure;
  a self-sealing septum coupled to the base structure to fluidly seal the upstream end of the cannula, wherein the self-sealing septum is maintained in position between the base structure and the lid assembly;
  a body-insertable physiological analyte sensor secured to and extending from the base structure, the sensor facilitating measurement of a physiological characteristic of the patient, and the sensor comprising a plurality of sensor leads; and
  an electronics assembly coupled to the base structure, the electronics assembly electrically connected to the sensor leads to obtain measurements of the physiological characteristic in an analog domain, and the electronics assembly comprising a digital processing circuit to convert measurements of the physiological characteristic from the analog domain into digital sensor data, to digitally process the digital sensor data into conditioned digital sensor data, and to communicate the conditioned digital sensor data to a fluid infusion device associated with the medical device component; and
 a top cover assembly that is removably couplable to the body-mountable base unit such that the top cover assembly covers the lid assembly of the body-mountable base unit, the top cover assembly comprising:
  a lid structure that releasably mates with the base structure, the lid structure comprising an interior space defined by an inner surface of the lid structure, and the lid structure comprising at least one structural support feature;
  an infusion tube secured to the inner surface of the lid structure and terminating within the interior space, wherein the at least one structural support feature of the lid structure receives, secures, and retains a downstream end of the infusion tube;
  a tubing connector fluidly coupled to the infusion tube, the tubing connector having a distal end supported by the at least one structural support feature of the lid structure, the distal end of the tubing connector penetrating the self-sealing septum to establish a fluid delivery flow path from inside the infusion tube, through the self-sealing septum, and into the cannula when the top cover assembly is coupled to the body-mountable base unit, wherein the self-sealing septum seals the upstream end of the cannula when the top cover assembly is removed from the body-mountable base unit and the tubing connector is withdrawn from the self-sealing septum;
a plurality of sensor conductors carried by or integrated with the infusion tube, the sensor conductors terminating within the interior space; and
an electrical interconnect assembly coupled to the inner surface of the lid structure, the electrical interconnect assembly establishing electrical connectivity between the sensor conductors and the electronics assembly when the top cover assembly is coupled to the body-mountable base unit, to facilitate communication of the conditioned digital sensor data from the electronics assembly to the fluid infusion device.

2. The medical device component of claim 1, the plurality of sensor leads comprising:
a reference conductor for a reference electrode of the sensor;
a working conductor for a working electrode of the sensor; and
a counter conductor for a counter electrode of the sensor.

3. The medical device component of claim 1, wherein:
the sensor conductors are embedded in tubing material of the infusion tube; and
terminating ends of the sensor conductors extend from an end of the infusion tube, and are exposed for connection to the electrical interconnect assembly.

4. The medical device component of claim 1, wherein:
the medical device component further comprises a connector assembly coupled to a second end of the infusion tube, the connector assembly being configured to fluidly couple the infusion tube to a fluid reservoir of the fluid infusion device, and to electrically couple the sensor conductors to an electronics module of the fluid infusion device.

5. The medical device component of claim 1, wherein:
the fluid infusion device is an insulin infusion pump;
the medical device component is an insulin infusion component;
the body-insertable physiological analyte sensor comprises a glucose sensor; and
the infusion tube is compatible with insulin medication fluid.

6. The medical device component of claim 1, the base unit further comprising a connector structure for the conditioned digital sensor data, the connector structure mating with electrical contact pads of the electrical interconnect assembly when the top cover assembly is coupled to the body-mountable base unit.

7. The medical device component of claim 6, wherein:
the connector structure comprises conductive elements corresponding to a power conductor, a ground conductor, and a data conductor for communication of the conditioned digital sensor data; and
the electrical contact pads of the electrical interconnect assembly physically contact the conductive elements of the connector structure when the top cover assembly is coupled to the body-mountable base unit.

8. The medical device component of claim 6, the connector structure comprising:
a pedestal extending from the body-mountable base unit; and
interconnection plugs positioned within the pedestal, the interconnection plugs formed from a conductive elastomeric material, wherein each of the interconnection plugs has a lower end electrically coupled to a corresponding conductive pad of the electronics assembly of the body-mountable base unit.

9. The medical device component of claim 6, further comprising a protective cap for the connector structure, the protective cap mating with and sealing the connector structure when the top cover assembly is removed from the body-mountable base unit.

10. The medical device component of claim 1, wherein the body-mountable base unit comprises:
a top surface;
a first hole formed in the top surface, the first hole accommodating the tubing connector, and the first hole accommodating a first insertion needle for inserting the cannula into skin of the patient; and
a second hole formed in the top surface, the second hole accommodating a second insertion needle for inserting the physiological analyte sensor into skin of the patient.

11. The medical device component of claim 1, wherein at least two of the sensor conductors carried by or integrated with the infusion tube provide operating power from the fluid infusion device to the electronics assembly when the top cover assembly is coupled to the body-mountable base unit.

12. The medical device component of claim 11, further comprising a battery that provides operating power to the electronics assembly when the top cover assembly is removed from the body-mountable base unit.

13. A medical device component for delivering medication fluid to a patient, the medical device component comprising:
a fluid infusion device to regulate delivery of medication fluid;
a base unit comprising:
a base structure;
a lid assembly affixed and sealed to the base structure;
a cannula that accommodates delivery of medication fluid as controlled by the fluid infusion device, the cannula having an upstream end securely attached to the base structure and having a downstream end extending from the base structure;
a self-sealing septum that fluidly seals the upstream end of the cannula, wherein the self-sealing septum is maintained in position between the base structure and the lid assembly;
a physiological analyte sensor that facilitates measurement of a physiological characteristic, the sensor comprising a plurality of sensor leads, the physiological analyte sensor secured to and extending from the base unit; and
an electronics assembly electrically connected to the sensor leads to obtain measurements of the physiological characteristic in an analog domain, and the electronics assembly comprising a digital processing circuit to convert measurements of the physiological characteristic from the analog domain into digital sensor data, to digitally process the digital sensor data into conditioned digital sensor data, and to communicate the conditioned digital sensor data to the fluid infusion device; and
a top cover assembly that is removably couplable to the base unit such that the top cover assembly covers the lid assembly of the base unit, the top cover assembly comprising:
a lid structure that releasably mates with the base unit, the lid structure comprising an interior space defined by an inner surface of the lid structure, and the lid structure comprising at least one structural support feature;

an infusion tube secured to the inner surface of the lid structure and terminating within the interior space, wherein the at least one structural support feature of the lid structure receives, secures, and retains a downstream end of the infusion tube;

a tubing connector fluidly coupled to the infusion tube, the tubing connector having a distal end supported by the at least one structural support feature of the lid structure, the distal end of the tubing connector penetrating the self-sealing septum to establish a fluid delivery flow path from inside the infusion tube, through the self-sealing septum, and into the cannula when the top cover assembly is coupled to the base unit, wherein the self-sealing septum seals the upstream end of the cannula when the top cover assembly is removed from the base unit and the tubing connector is withdrawn from the self-sealing septum;

a plurality of sensor conductors terminating within the interior space; and an electrical interconnect assembly coupled to the inner surface of the lid structure, the electrical interconnect assembly establishing electrical connectivity between the sensor conductors and the electronics assembly when the top cover assembly is coupled to the base unit, to facilitate communication of the conditioned digital sensor data from the electronics assembly to the fluid infusion device.

14. The medical device component of claim 13, wherein:
the sensor conductors are carried by or integrated with the infusion tube; and
terminating ends of the sensor conductors extend from an end of the infusion tube, and are exposed for connection to the electrical interconnect assembly.

15. The medical device component of claim 13, wherein:
the medical device component further comprises a connector assembly coupled to a second end of the infusion tube, the connector assembly being configured to fluidly couple the infusion tube to a fluid reservoir of the fluid infusion device, and to electrically couple the sensor conductors to an electronics module of the fluid infusion device.

16. The medical device component of claim 13, the base unit further comprising a connector structure for the conditioned digital sensor data, the connector structure mating with electrical contact pads of the electrical interconnect assembly when the top cover assembly is coupled to the base unit.

17. The medical device component of claim 13, wherein the base unit comprises:
a top surface;
a first hole formed in the top surface, the first hole accommodating the tubing connector, and the first hole accommodating a first insertion needle for inserting the cannula into skin of the patient; and
a second hole formed in the top surface, the second hole accommodating a second insertion needle for inserting the physiological analyte sensor into skin of the patient.

18. The medical device component of claim 13, wherein at least two of the sensor conductors provide operating power from the fluid infusion device to the electronics assembly when the top cover assembly is coupled to the base unit.

19. The medical device component of claim 18, further comprising a battery that provides operating power to the electronics assembly when the top cover assembly is removed from the base unit.

* * * * *